US005939422A

United States Patent [19]

Cavalla et al.

[11] Patent Number: 5,939,422
[45] Date of Patent: Aug. 17, 1999

[54] CHEMICAL COMPOUNDS HAVING PDE-IV INHIBITION ACTIVITY

[75] Inventors: David Cavalla, Cambridge, United Kingdom; Anddre Gehrig, Basel, Switzerland; Mark Chasin, Manalapan, N.J.; Peter Hofer, Liestal; Peter Wintergest, Basel, both of Switzerland

[73] Assignee: Euro-Celtique, S.A., Luxembourg, Luxembourg

[21] Appl. No.: 08/578,580

[22] PCT Filed: Jun. 21, 1994

[86] PCT No.: PCT/GB94/01334

§ 371 Date: Apr. 8, 1996

§ 102(e) Date: Apr. 8, 1996

[87] PCT Pub. No.: WO95/00516

PCT Pub. Date: Jan. 5, 1995

[30] Foreign Application Priority Data

Jun. 22, 1993 [GB] United Kingdom .................... 9312853

[51] Int. Cl.$^6$ .................... A61K 31/52; C07D 473/34; C07D 473/24
[52] U.S. Cl. .................... 514/261; 514/266; 544/276; 544/277
[58] Field of Search .................... 544/277, 276; 514/261, 266

[56] References Cited

U.S. PATENT DOCUMENTS

| Re. 31,429 | 10/1983 | Tull et al. | 544/277 |
|---|---|---|---|
| 2,320,654 | 6/1943 | Riester | 95/7 |
| 2,691,654 | 10/1954 | Hitchings | 544/277 |
| 2,844,577 | 7/1958 | Acker | 544/277 |

(List continued on next page.)

FOREIGN PATENT DOCUMENTS

| 994351 | 8/1976 | Canada . | |
|---|---|---|---|
| 0018136 | 10/1980 | European Pat. Off. . | |
| 0178413 | 4/1986 | European Pat. Off. | C07D 235/18 |
| 0191313 | 8/1986 | European Pat. Off. . | |
| 0203721 | 12/1986 | European Pat. Off. . | |
| 0256692 | 2/1988 | European Pat. Off. . | |
| 256692 | 2/1988 | European Pat. Off. . | |
| 0258191 | 3/1988 | European Pat. Off. . | |
| 0343643 | 11/1989 | European Pat. Off. | A61K 31/41 |
| 360701 | 3/1990 | European Pat. Off. . | |

(List continued on next page.)

OTHER PUBLICATIONS

G. Elion, "Some New N–Methylpurines," Chem. Found. Symp. Chem. Biol. Purines, 1957, pp. 39–49.
Glusenkamp, Karl–Heinz, et al., "Tautomer–Specific Anti–(N–3–Substituted)–Adenine Antibodies: New Tools in Molecular Dosimetry and Epidemiology", Angew. Chem. Int. Ed. Engl. 1993, 32, No. 11, pp. 1640–1641.
CA Select: "Anti–Inflammatory Agents & Arthritis" Issue 7, 1996, p. 26.

Abstract of PCT Gazette—Section I, No. 26/19 of WO 96/16657.
Abstract of JP 6–192244 (1 page) 1994.
CA Selects: "Allergy & Antiallergic Agents", 1996 CA 124:85064a); 124:87030.
CA Selects: "Allergy & Antiallergic Agents", Issue 21, 1995, p. 13 CA 123:169644.
CA Selects: Anti–Inflammatory Agents & Arthritis, Issue 23, 1995, pp. 17 and 23 CA 123:228202, 123, 227818.
CA Selects: "Anti–Inflammatory Agents & Arthritis", Issue 25, 1996, (1 page) CA 125:275430.
CA 171494, 171495 and KG–2683 of Annual Drug Data Report 1991 (1 sheet).
Derwent Abstract of DE4309969 (1994).
Ronald E. Weishaar, et al.., Subclass of Cyclic GMP–Specific phosphodiesterase and their role in regulating the effects of atrial natriuretic factor, Dept. Of Pharmacology, Parke–Davis Pharmaceutical Research Division, Warner–Lambert Co. Hypertension, vol. 15, No. 5, May 1990.
"Differential modulation of tissue function and therapeutic potential selective inhibitors of cyclic nucleotide phosphodiesterase isoenzymes", C. David Nicholson, R.A. John Chaliss and Mohammed Shahid, 1991, Elsevier Science Publishers Ltd. (UK), TIPS 12:19–27.

(List continued on next page.)

Primary Examiner—Mark L Berch
Attorney, Agent, or Firm—Davidson, Davidson & Kappel, LLC

[57] ABSTRACT

Disclosed is a compound of the formula (I):

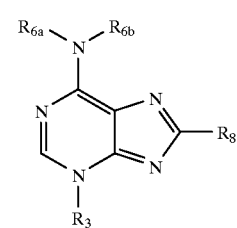

wherein
  $R_3$, $R_{6a}$ and $R_8$ are the same or different and represent a $C_{2-8}$ alkyl which is unbranched or branched and unsubstituted or substituted; $C_{3-8}$ cycloalkyl which is unsubstituted or substituted; $C_{4-8}$ cycloalkylalkyl wherein the cycloalkyl portion is unsubstituted or substituted; aryl which is unsubstituted or substituted; aralkyl $C_{1-4}$; heterocyclyl; and heterocyclylalkyl ($C_1$–$C_4$)
  $R_{6b}$ represents H or $R_{6a}$, or together $R_{6b}$, N, and $R_{6a}$ make a $C_3$–$C_8$ ring containing from one to three nitrogen atoms, from zero to two oxygen atoms, from zero to two sulfur atoms, which is optionally substituted;
and where aryl is phenyl or naphthyl, the heterocyclyl is a 5, 6 or 7 membered ring including from one to three nitrogen atoms, and from zero to two oxygen atoms, from zero to two sulfur atoms, and can be substituted as in aryl on the carbons or nitrogens of that ring;
or a pharmaceutically acceptable salt thereof.

50 Claims, 2 Drawing Sheets

U.S. PATENT DOCUMENTS

| | | | |
|---|---|---|---|
| 2,903,455 | 9/1959 | Strong | 544/277 |
| 2,956,998 | 10/1960 | Baizer | 544/277 |
| 2,957,875 | 10/1960 | Lyttle | 544/277 |
| 2,966,488 | 12/1960 | Shive | 544/277 |
| 3,079,378 | 2/1963 | Schroeder | 260/211.5 |
| 3,129,225 | 4/1964 | Shapiro | 260/247.2 |
| 3,135,753 | 6/1964 | Hitchings | 540/265 |
| 3,136,771 | 6/1964 | Liechti et al. | 260/549 |
| 3,215,696 | 11/1965 | Denayer | 544/277 |
| 3,225,046 | 12/1965 | Zwahlen | 544/277 |
| 3,262,929 | 7/1966 | Okubu et al. | 260/240 |
| 3,470,164 | 9/1969 | Takamatsu | 260/240 |
| 3,491,091 | 1/1970 | Berger | 260/240 |
| 3,491,106 | 1/1970 | Freyermuth | 260/304 |
| 3,494,919 | 2/1970 | Collins et al. | 260/240 |
| 3,516,997 | 6/1970 | Takano et al. | 260/243 |
| 3,541,100 | 11/1970 | Ramirez et al. | 260/286 |
| 3,551,554 | 12/1970 | Herschler | 424/7 |
| 3,574,218 | 4/1971 | Hideg et al. | 260/293.4 |
| 3,586,670 | 6/1971 | Brenneisen | 260/240 |
| 3,590,029 | 6/1971 | Koch | 260/211.5 |
| 3,626,018 | 12/1971 | Taylor | 260/670 |
| 3,636,039 | 1/1972 | Gruenman et al. | 260/309.7 |
| 3,647,812 | 3/1972 | Smith | 260/304 |
| 3,658,799 | 4/1972 | Eardley | 260/243 C |
| 3,666,769 | 5/1972 | Jones | 260/304 |
| 3,669,979 | 6/1972 | Freyermuth | 260/304 |
| 3,674,781 | 7/1972 | Schinzel et al. | 260/240 |
| 3,681,328 | 8/1972 | Kurita | 260/243 C |
| 3,686,238 | 8/1972 | Zaffaroni | 260/399 |
| 3,706,834 | 12/1972 | Scheilenbaum et al. | 424/272 |
| 3,923,833 | 12/1975 | Gruenman et al. | 260/340.5 |
| 3,962,452 | 6/1976 | Evans et al. | 424/272 |
| 4,020,165 | 4/1977 | Hubbard | 514/367 |
| 4,025,636 | 5/1977 | Dunwell et al. | 424/269 |
| 4,025,637 | 5/1977 | Dunwell et al. | 424/272 |
| 4,107,306 | 8/1978 | Voorhees | 424/248.51 |
| 4,146,721 | 3/1979 | Rainer | 548/374 |
| 4,167,628 | 9/1979 | Kormany | 542/454 |
| 4,233,303 | 11/1980 | Bergstrand et al. | 424/253 |
| 4,241,063 | 12/1980 | Naito et al. | 424/253 |
| 4,241,168 | 12/1980 | Arai | 430/503 |
| 4,308,278 | 12/1981 | Schneider et al. | 424/273 |
| 4,361,699 | 11/1982 | Rasmusson et al. | 544/277 |
| 4,407,802 | 10/1983 | Graham et al. | 424/253 |
| 4,416,892 | 11/1983 | Dawson | 424/272 |
| 4,454,138 | 6/1984 | Goring | 424/253 |
| 4,469,698 | 9/1984 | Philippossian et al. | 424/253 |
| 4,495,195 | 1/1985 | Beck et al. | 514/406 |
| 4,616,020 | 10/1986 | Furrer et al. | 514/264 |
| 4,652,654 | 3/1987 | Verga et al. | 548/217 |
| 4,684,656 | 8/1987 | Atwal | 514/274 |
| 4,684,728 | 8/1987 | Möhring | 544/182 |
| 4,710,503 | 12/1987 | Hofer | 514/263 |
| 4,732,978 | 3/1988 | Kreft et al. | 546/152 |
| 4,755,517 | 7/1988 | Bruns et al. | 514/263 |
| 4,757,124 | 7/1988 | Koyanagi | 526/62 |
| 4,769,377 | 9/1988 | Snyder et al. | 514/263 |
| 4,770,990 | 9/1988 | Nakamura | 430/564 |
| 4,803,216 | 2/1989 | Appleton et al. | 514/207 |
| 4,810,719 | 3/1989 | Appleton et al. | 514/406 |
| 4,826,868 | 5/1989 | Wachter et al. | 514/407 |
| 4,831,152 | 5/1989 | Itoh et al. | 548/224 |
| 4,851,321 | 7/1989 | Takagi | 430/264 |
| 4,868,183 | 9/1989 | Kanai et al. | 514/255 |
| 4,874,869 | 10/1989 | Ueda et al. | 548/309 |
| 4,883,801 | 11/1989 | Nathanson | 514/263 |
| 4,910,211 | 3/1990 | Imamura et al. | 514/367 |
| 4,918,074 | 4/1990 | Tsuda et al. | 514/258 |
| 4,925,847 | 5/1990 | Hofer | 514/263 |
| 4,965,169 | 10/1990 | Hirano | 430/264 |
| 4,971,972 | 11/1990 | Doll et al. | 514/265 |
| 4,981,857 | 1/1991 | Daluge | 574/263 |
| 4,994,363 | 2/1991 | Koya et al. | 430/564 |
| 5,010,081 | 4/1991 | Hofer | 514/263 |
| 5,047,411 | 9/1991 | Takasugi et al. | 514/300 |
| 5,057,517 | 10/1991 | Johnston et al. | 514/254 |
| 5,068,236 | 11/1991 | Suzuki et al. | 514/263 |
| 5,091,431 | 2/1992 | Tulshian et al. | 514/262 |
| 5,098,464 | 3/1992 | Barton et al. | 71/92 |
| 5,110,818 | 5/1992 | Allgeier | 514/261 |
| 5,114,835 | 5/1992 | Sakanoue | 430/393 |
| 5,116,717 | 5/1992 | Matsushita | 430/264 |
| 5,117,830 | 6/1992 | McAfee | 128/654 |
| 5,139,921 | 8/1992 | Takagi et al. | 430/264 |
| 5,177,074 | 1/1993 | Allen et al. | 514/234 |
| 5,190,942 | 3/1993 | Poss | 514/235.8 |
| 5,191,084 | 3/1993 | Bagli et al. | 546/279 |
| 5,206,255 | 4/1993 | Ubasawa et al. | 514/374 |
| 5,264,589 | 11/1993 | Corey | 548/51 |
| 5,270,206 | 12/1993 | Saccomano | 435/280 |
| 5,288,896 | 2/1994 | Capiris et al. | 560/27 |
| 5,290,782 | 3/1994 | Suzuki et al. | 514/263 |
| 5,322,847 | 6/1994 | Marfat et al. | 514/303 |
| 5,342,835 | 8/1994 | Pepin et al. | 514/227.5 |
| 5,424,432 | 6/1995 | Fredenburgh et al. | 546/118 |
| 5,434,150 | 7/1995 | Austel et al. | 514/228.5 |
| 5,436,258 | 7/1995 | Blake et al. | 514/372 |
| 5,449,686 | 9/1995 | Christensen, IV | 514/330 |
| 5,451,596 | 9/1995 | Ullrich | 514/349 |
| 5,496,853 | 3/1996 | Shiota et al. | 514/469 |
| 5,602,157 | 2/1997 | Christensen, IV | 514/362 |
| 5,602,173 | 2/1997 | Christensen, IV | 514/475 |
| 5,631,260 | 5/1997 | Belardinelli et al. | 514/263 |

FOREIGN PATENT DOCUMENTS

| | | | |
|---|---|---|---|
| 0369744 | 5/1990 | European Pat. Off. | |
| 0386683 | 9/1990 | European Pat. Off. | |
| 0389282 | 9/1990 | European Pat. Off. | |
| 0400799 | 12/1990 | European Pat. Off. | |
| 0435811 | 7/1991 | European Pat. Off. | |
| 0463756 | 1/1992 | European Pat. Off. | |
| 0470805 | 2/1992 | European Pat. Off. | C07C 271/60 |
| 0497564 | 8/1992 | European Pat. Off. | C07C 235/36 |
| 0511865 | 11/1992 | European Pat. Off. | |
| 0536713 | 4/1993 | European Pat. Off. | |
| 0590919 | 4/1994 | European Pat. Off. | |
| 0619316 | 10/1994 | European Pat. Off. | |
| 0623607 | 11/1994 | European Pat. Off. | |
| 0645389 | 3/1995 | European Pat. Off. | |
| 0671389 | 9/1995 | European Pat. Off. | |
| 0675124 | 10/1995 | European Pat. Off. | |
| 0685474 | 12/1995 | European Pat. Off. | |
| 0685479 | 12/1995 | European Pat. Off. | |
| 0728759 | 8/1996 | European Pat. Off. | |
| 0731099 | 9/1996 | European Pat. Off. | |
| 0779291 | 6/1997 | European Pat. Off. | |
| 835818 | 2/1961 | France . | |
| 1548252 | 10/1968 | France . | |
| 2104932 | 6/1972 | France . | |
| 2008464 | 9/1970 | Germany . | |
| 2314676 | 10/1973 | Germany . | |
| 2346034 | 4/1974 | Germany . | |
| 51-54587 | 5/1976 | Japan . | |
| 57-21375 | 2/1982 | Japan . | |
| 559056 | 3/1993 | Japan . | |
| 6211856 | 8/1994 | Japan . | |
| 7118247 | 5/1995 | Japan . | |
| 717952 | 7/1995 | Japan . | |
| 8113567 | 5/1996 | Japan . | |
| 215948 | 10/1989 | New Zealand . | |

| | | |
|---|---|---|
| 1077689 | 8/1967 | United Kingdom . |
| 1260793 | 1/1972 | United Kingdom . |
| 1498705 | 1/1978 | United Kingdom ......... C07D 207/26 |
| 1561005 | 2/1980 | United Kingdom . |
| 2041359 | 9/1980 | United Kingdom . |
| 1580782 | 12/1980 | United Kingdom . |
| 2283488 | 5/1995 | United Kingdom . |
| 8601724 | 3/1986 | WIPO . |
| 8706576 | 4/1986 | WIPO . |
| 9631487 | 10/1986 | WIPO . |
| 9100858 | 1/1991 | WIPO . |
| 9200968 | 1/1992 | WIPO . |
| 9205175 | 4/1992 | WIPO . |
| 9205176 | 4/1992 | WIPO . |
| 9207567 | 5/1992 | WIPO . |
| WO9219594 | 11/1992 | WIPO . |
| 9307141 | 4/1993 | WIPO . |
| WO9307111 | 4/1993 | WIPO . |
| WO9314081 | 7/1993 | WIPO . |
| WO9314082 | 7/1993 | WIPO . |
| WO9315044 | 8/1993 | WIPO . |
| WO9315045 | 8/1993 | WIPO . |
| 9318024 | 9/1993 | WIPO . |
| 9319749 | 10/1993 | WIPO . |
| 9319750 | 10/1993 | WIPO . |
| 9319751 | 10/1993 | WIPO . |
| WO9319747 | 10/1993 | WIPO . |
| 9322287 | 11/1993 | WIPO . |
| WO9325517 | 12/1993 | WIPO . |
| WO9402465 | 2/1994 | WIPO . |
| WO9410118 | 5/1994 | WIPO . |
| WO9412461 | 6/1994 | WIPO . |
| WO9414742 | 7/1994 | WIPO . |
| WO9414800 | 7/1994 | WIPO . |
| 9420460 | 9/1994 | WIPO . |
| WO9420446 | 9/1994 | WIPO . |
| WO9420455 | 9/1994 | WIPO . |
| 9422859 | 10/1994 | WIPO . |
| 9425437 | 11/1994 | WIPO . |
| 9500139 | 1/1995 | WIPO . |
| 9501338 | 1/1995 | WIPO . |
| 9503297 | 2/1995 | WIPO . |
| 9503794 | 2/1995 | WIPO . |
| 9504045 | 2/1995 | WIPO . |
| 9504046 | 2/1995 | WIPO . |
| 9508534 | 3/1995 | WIPO . |
| 9509623 | 4/1995 | WIPO . |
| 9509624 | 4/1995 | WIPO . |
| 9509627 | 4/1995 | WIPO . |
| 9509836 | 4/1995 | WIPO . |
| 9509837 | 4/1995 | WIPO . |
| 9604253 | 5/1995 | WIPO . |
| 9514667 | 6/1995 | WIPO . |
| 9517386 | 6/1995 | WIPO . |
| 9517392 | 6/1995 | WIPO . |
| 9517399 | 6/1995 | WIPO . |
| 9522520 | 8/1995 | WIPO . |
| 9523148 | 8/1995 | WIPO . |
| 9527692 | 10/1995 | WIPO . |
| 9535281 | 12/1995 | WIPO . |
| 9535282 | 12/1995 | WIPO . |
| 9535283 | 12/1995 | WIPO . |
| 9535284 | 12/1995 | WIPO . |
| 9535285 | 12/1995 | WIPO . |
| 9600215 | 1/1996 | WIPO . |
| 9603396 | 2/1996 | WIPO . |
| 9603399 | 2/1996 | WIPO . |
| 9612720 | 5/1996 | WIPO . |
| 9620157 | 7/1996 | WIPO . |
| 9620158 | 7/1996 | WIPO . |
| 9620174 | 7/1996 | WIPO . |
| 9620175 | 7/1996 | WIPO . |
| 9624350 | 8/1996 | WIPO . |
| 9631476 | 10/1996 | WIPO . |
| 9631485 | 10/1996 | WIPO . |
| 9631486 | 10/1996 | WIPO . |
| 9628430 | 11/1996 | WIPO . |
| 9636595 | 11/1996 | WIPO . |
| 9636596 | 11/1996 | WIPO . |
| 9636611 | 11/1996 | WIPO . |
| 9636624 | 11/1996 | WIPO . |
| 9636625 | 11/1996 | WIPO . |
| 9636626 | 11/1996 | WIPO . |
| 9636638 | 11/1996 | WIPO . |
| 9638150 | 12/1996 | WIPO . |
| 9703070 | 1/1997 | WIPO . |
| 9703967 | 2/1997 | WIPO . |
| 9712887 | 4/1997 | WIPO . |
| 9712888 | 4/1997 | WIPO . |
| 9720833 | 6/1997 | WIPO . |
| 9722585 | 6/1997 | WIPO . |
| 9722586 | 6/1997 | WIPO . |
| 9723457 | 7/1997 | WIPO . |
| 9723460 | 7/1997 | WIPO . |
| 9723461 | 7/1997 | WIPO . |
| 9724334 | 7/1997 | WIPO . |
| 9725312 | 7/1997 | WIPO . |
| 9728143 | 8/1997 | WIPO . |
| 9728144 | 8/1997 | WIPO . |
| 9728145 | 8/1997 | WIPO . |
| 9728146 | 8/1997 | WIPO . |
| 9728147 | 8/1997 | WIPO . |
| 9728148 | 8/1997 | WIPO . |
| 9728155 | 8/1997 | WIPO . |

OTHER PUBLICATIONS

"Phosphodiesterase inhibitors: new opportunities for the treatment of asthma", Theodore J. Torphy, Bradley J. Undem, *Thorax* 1991; 46:512–523.

"Novel phosphodiesterase inhibitors for the therapy of asthma", Theodore J. Torphy, George P. Livi and Siegfried B. Christensen, DN&P 6(4), May 1993 pp. 203–214

"Assay of cyclic nucleotide phosphodiesterase and resolution of multiple molecular forms of the enzyme", W. Joseph Thompson, Wesley L. Terasaki, Paul M. Epstein, Samuel J. Strada, Advances in Cyclic Nucleotide Research, vol. 10, 1979, p. 69–92.

"Identification, characterization and functional role of phosphodiesterase isozymes in human airway smooth muscle", Theodore J. Torphy, Bradley J. Undem, Lenora B. Cieslinski, Mark A. Luttmann, Martin L. Reeves and Douglas W.P. Hay, The Journal of Pharmacology and Experimental Therapeutics, 1993, vol. 265, No. 3, 1213–1223.

"The PDE IV family of calcium–independent phosphodiesterase enzymes", John A. Lowe III and John B. Cheng, Drugs of the Future, 1992, 17(9):799–807.

"Could isoenzyme–selective phosphodiesterase inhibitors render bronchodilator therapy redundant in the treatment of bronchial asthma?", Mark A. Giembycz, Biochemical Pharmacology, 1992, vol. 43, No. 10 pp. 2041–2051.

"Differential pharmacologic sensitivity of cyclic nucleotide phosphodiesterase isozymes from cardiac muscle, arterial and airway smooth muscle", Paul J. Silver, Linda T. Hamel, Mark H. Perrone, Ross G. Bently, Cynthia R. Bushover and Dale B. Evans, European Journal of Pharmacology, 150(1988) 85–94, Elsevier.

"The pharmacology and therapeutic use of theophylline", Miles Weinberger, M.D., The Journal of Allergy and Clinical Immunology, vol. 73, No. 5, Part 1, 525–544 (1984).

"Structure–Activity Relationships in a Series of 6–Thioxanthines with Bronchodilator and Coronary Dilator Properties", A.K. Armitrage, Janet Boswood and B.J. Large, Brit. J. Pharma. 1961, 17:196–207.

"The Synthesis of Some 6 Thioxanthines", K.R.H. Wooldrige and R. Slack, J. Chem. Soc. 1962, Annex IV:1863–1868.

Isomura et al., "Studies on the synthesis and anti–inflammatory activity of 2,6–Di–tert–butylphenols with a heterocyclic group at the 4–position.I", vol. 31, No. 9, pp. 3168–3178 (1983).

CA 103:37354, 1985 (Nagarajan). 1984.

CA 116:255335, 1992 (Bender). 1992.

CA 88: 51054, 1977 (Ninomiya). 1978.

Chem. Abstracts, vol. 82(19) May 12, 1975, Abstract #125358x.

CA 114:246982, 1990 (Naruto). (1991).

CA 92: 6207, 1977 (Pirsino). 1980.

Ronald E. Weishaar, et al., Multiple molecular forms of cyclic nucleotide phosphodiesterase in cardiac and smooth muscle and in platelets, Biochemical Pharmacology, vol. 35, No. 5., pp. 787–800, 1986.

CA 75:No. 7, Aug. 16, 1971, 49027b; with corresponding article entitled Synthesis of 3–Methylisoguanine (6–amino–3–methylpurin–2(3H)–one) G.T. Rogers and T.L.V. Ulbricht, J. Chem. Soc. (C), pp. 2364–2366, 1971.

"Controlled Interaction between Nucleic Acid Bases. Intramolecular Stacking Interactions between Two Adenine Rings", Nelson J. Leonard, et al.; Journal of the American Chemical Society, 95:12, Jun. 13, 1973, pp. 4010–4016.

Burger, Ed. "Medicinal Chemistry" 2d ed. pp. 42–43, Interscience, New York, New York (1960).

Ram et al., Indian J. Chem., Sect. B (1993), 32B(9), 924–8.

Salem et al., CA 117:26410 (1992).

Ram et al., CA 116:6463 (1992).

Nikolyukin et al., CA 114:122145 (1991).

Pepin et al., CA 114:96801 (1991).

Murray ey al., CA 112:198208 (1990).

Agrawal, CA 109:54701 (1988).

Tominaga et al., CA 107:236648 (1987).

Vishwakarma et al., CA 104:168404 (1986).

Reddy et al., CA 104:168228 (1986).

Feeny, CA 92:17174 (1980).

De Lucia et al., CA 68:96797 (1968).

Derwent Abstract of JP 1200246, published Aug. 11, 1989.

Derwent Abstract of JP 1245256, published Sep. 29, 1989.

Derwent Abstract of JP 1231049, published Sep. 14, 1989.

Derwent Abstract of JP 1229251, published Sep. 12, 1989.

Derwent Abstract of JP 1225951, published Sep. 8, 1989.

Derwent Abstract of JP 1224756, published Sep. 7, 1989.

Derwent Abstract of JP 1224755, published Sep. 7, 1989.

Derwent Abstract of JP 1219748, published Sep. 1, 1989.

Derwent Abstract of JP 1216353, published Aug. 20, 1989.

Derwent Abstract of JP 1214845, published Aug. 29, 1989.

Derwent Abstract of JP 1093733, published Apr. 12, 1989.

Derwent Abstract of JP 63271246, published Nov. 9, 1988.

Derwent Abstract of DE 144519 Aug. 31, 1993.

Derwent Abstract of JP 58111034, published Jul. 1, 1983.

Reitz, J.Org. Chem 55, 5761 (1990.

Itaya, Zet. Letters 23, 2203 (1982).

Enoki, Chem Abs 85, 5692(1976.

Kazimierczuk, Chem Abs 82, 125358 (1974).

Ulbricht, Chem Abs 75, 49027b (1971).

Aida, Chem Abs 86, 43746 (1976).

Enoki, Chem Abs 84, 180299 (1976).

Girshovich, Chem Abs 116, 173873 (1991).

Montgomery, J.A.C.S. 81, 3963 (1959).

Elion, Chem Abs 53, 6243h (1957).

Fuji, J. Med. Chem 22, 125 (1979).

5,939,422

CHEMICAL COMPOUNDS HAVING PDE-IV INHIBITION ACTIVITY

This application is a national stage application of International application PCT/GB94/01334, filed Jun. 21, 1994, under 35 U.S.C. § 371.

BACKGROUND OF THE INVENTION

The present invention relates to purine derivatives, to processes for their preparation, to pharmaceutical compositions containing them and to their medical use. In particular the invention relates to 3-substituted and 3,8-disubstituted 6-amino purine derivatives having bronchial and tracheal relaxation and/or anti-inflammatory activity. The invention is also related to the thioisoguanine and dithioxanthine precursor compounds of these purine derivatives, to pharmaceutical compositions containing them and to their medical use.

Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular cyclic adenosine 3',5'-cyclicmonophosphate (cAMP) or guanosine 3',5'-cyclicmonophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterases Inhibitors For The Therapy Of Asthma", Drug News & Prospectives, 6(4) May 1993, pages 203–214. The PDE enzymes can be grouped into five or more families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and possesses positive inotropic activity. PDE IV is cAMP specific, and possesses airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited.

It has previously been shown that the 3,8-disubstituted 6-thioxanthine derivatives as described in EP-A-0256692 exhibit enhanced bronchodilator and anti-inflammatory activity compared to the corresponding xanthine derivatives. Transformation of these 6-thioxanthine derivatives to the corresponding thioisoguanines substantially reduces the bronchodilator and anti-inflammatory activity in certain tests.

PDE IV (and possibly PDE V) is present in all the major inflammatory cells in asthma including eosinophils, neutrophils, T-lymphocytes, macrophages and endothelial cells. Its inhibition causes down regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and anti-inflammatory properties would be most advantageous. It appears that selective PDE IV inhibitors should be more effective with fewer side effects than theophylline. Clinical support has been shown for this hypothesis. Attempts have therefore been made to find new compounds having more selective and improved PDE IV inhibition.

Surprisingly, the present inventors have found that the analogous transformation of 3 and 3,8-disubstituted thiohypoxanthines, which themselves usually exhibit little if any PDE IV inhibitory activity, to the corresponding purine derivatives gives compounds having PDE IV inhibitory activity comparable to or in some cases greater than 6-thioxanthine derivatives of EP-A-0256692.

A different preparation of 3-methyl-6-dimethylamino-3H-purine, 3-benzyl-6-methylamino-3H-purine and 3-benzyl-6-isopropylamino-3H-purine was reported in J. Org. Chem., 55, 5761–5766 (1990). No biological activity was disclosed for these compounds.

OBJECTS AND SUMMARY OF THE INVENTION

It is accordingly a primary object of the present invention to provide new compounds which are effective PDE IV inhibitors.

It is another object of the present invention to provide new compounds which act as effective PDE IV inhibitors with lower PDE III inhibition.

It is another object of the present invention to provide a method of synthesizing the new compounds of this invention.

It is another object of the present invention to provide a method of treating a patient requiring PDE IV inhibition.

It is another object of the present invention to provide a method for treating a mammal suffering from a disease state selected from the group consisting of asthma, allergies, inflammation, depression, dementia and disease states associated with abnormally high physiological levels of cytokine (s) such as tumor necrosis factor.

DETAILED DESCRIPTION

Figure 1:
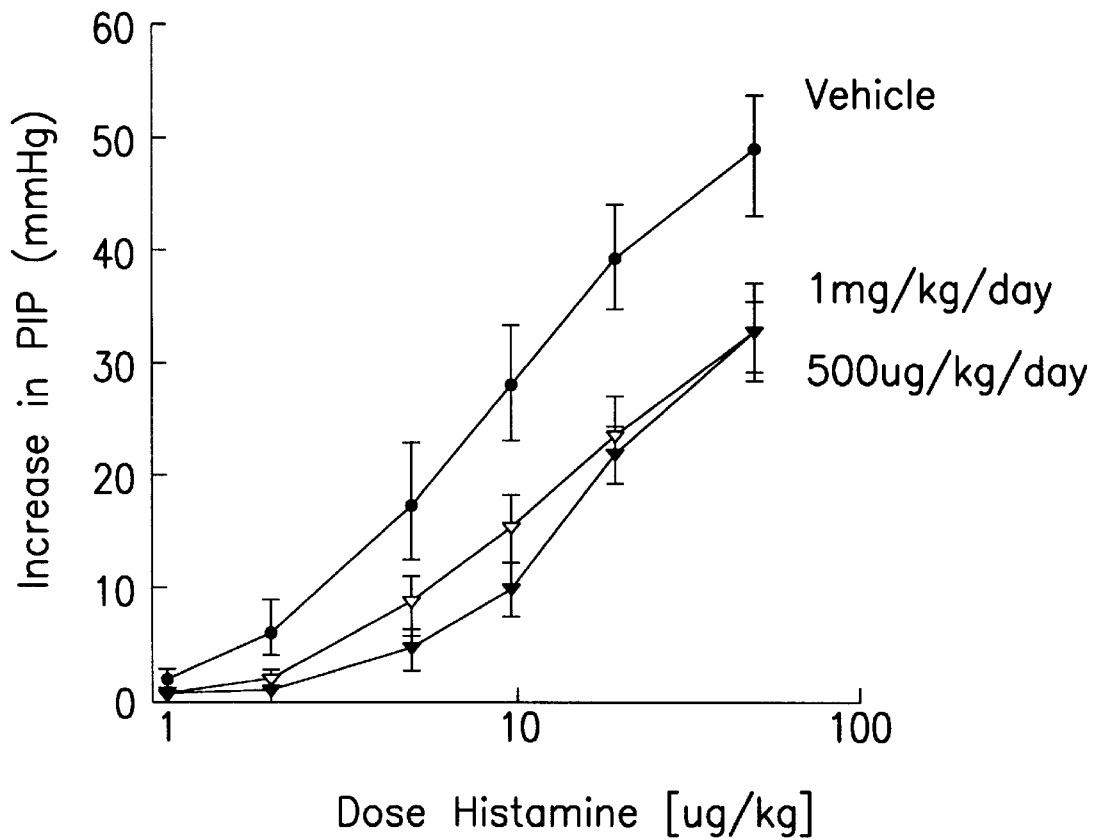
FIG. 1 shows dose response curves to histamine in a test animal after administration of 8-cyclopropyl-3-ethyl-6-ethylamino-3H-purine at doses of 0.5 and 1.0 mg/kg/day given subcutaneously over 7 days by osmotic mini-pump.

With the above and other objects in view, the present invention relates in part to a novel group of 3-substituted and 3,8-disubstituted 6-amino purine derivatives having bronchodilator and/or anti-inflammatory activity.

The present invention therefore provides a compound of formula (I)

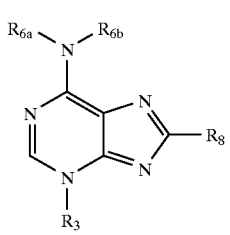

wherein $R_3$, $R_{6a}$ and $R_8$ are the same or different and each represent a H or $C_{1-8}$ alkyl which is unbranched or branched and unsubstituted or substituted with OH, alkoxy, halogen, =NOH, =NOCONH$_2$, or =O ; $C_{3-8}$ cycloalkyl which is unsubstituted or substituted with OH, alkoxy, halogen, haloalkyl, halogen, =NOH, =NOCONH$_2$, or =O; $C_{4-8}$ cycloalkylalkyl wherein the cycloalkyl portion is unsubstituted or substituted with one or more OH, alkoxy, halogen, =NOH, =NOCONH$_2$, or =O; aryl which is unsubstituted or substituted with one or more of halogen, NH$_2$, alkylamino, dialkylamino, $C_1$–$C_8$ acylamino, $C_{1-8}$ alkylsulfonylamino, optionally substituted carbamyl, OH, $C_1$–$C_6$ alkoxy, $C_3$–$C_8$ cycloalkoxy, C=NOH, C=NOCONH$_2$, $C_1$–$C_8$ alkyl, phenyl or benzyl; aralkyl $(C_1$–$_4)$; heterocyclyl; heterocyclylalkyl $(C_1$–$C_4)$; heteroaryl; and heteroaralkyl;

$R_{6b}$ represents a H or $R_{6a}$, or together $R_{6b}$, N, and $R_{6a}$ make a $C_3$–$C_8$ membered ring containing from one to three nitrogen atoms, from zero to two oxygen atoms, from zero to two sulfur atoms, optionally substituted with alkoxy, CO$_2$H, CONH$_2$, =NOH, =NOCONH$_2$, =O;

and where aryl is phenyl or naphthyl, the heterocyclyl is a 5, 6 or 7 membered ring including from one to three nitrogen atoms, one or two oxygen atoms, zero to two sulfur atoms, and can be substituted as in aryl on the carbons or nitrogens of that ring;

or a pharmaceutically acceptable salt thereof provided that when $R_3$ is a benzyl group, $R_{6a}$ is a methyl or isopropyl group and $R_{6b}$ is a hydrogen atom or $R_3$, $R_{6a}$ and $R_{6b}$ are methyl groups, $R_8$ is other than a hydrogen atom.

In certain preferred embodiments, $R_3$ represents a $C_{1-8}$ alkyl, $C_{3-7}$ cycloalkyl, $C_{4-8}$ cycloalkylalkyl, aryl or ar($C_{1-4}$) alkyl group; heteroaryl or heteroar($C_{1-4}$)alkyl;

$R_{6a}$ represents a $C_{1-8}$ alkyl, $C_{3-7}$ cycloalkyl, $C_{4-8}$ cycloalkylalkyl, aryl, ar($C_{1-4}$)alkyl group, or heterocyclyl $(C_{1-4})$alkyl group; $R_{6b}$ represents a hydrogen atom or a $C_{1-8}$ alkyl, $C_{3-7}$ cycloalkyl, $C_{4-8}$ cycloalkylalkyl, aryl or ar($C_{1-4}$) alkyl group; or —NR$_{6a}$R$_{6b}$ together forms a 5-membered or 6-membered ring, which ring optionally contains one or more additional heteroatoms; and $R_8$ represents a hydrogen atom or a $C_{1-8}$ alkyl, $C_{3-7}$ cycloalkyl, $C_{4-8}$ cycloalkylalkyl, aryl, ar($C_{1-4}$)alkyl, pyridyl or pyridyl($C_{1-4}$)alkyl group.

For purposes of the present invention, as used herein, a $C_{1-8}$ alkyl group or the $C_{1-4}$ alkyl moiety of an ar($C_{1-4}$) alkyl, or heterocyclo($C_{1-4}$)alkyl group may be straight or branched chain and may be substituted or unsubstituted. A $C_{1-8}$ alkyl group is preferably a $C_{1-5}$ alkyl group and for example methyl, ethyl, n-propyl, iso-propyl, n-butyl, isobutyl or isopentyl. Suitable substituents include hydroxy, alkoxy (for example methoxy or ethoxy), halogen (for example fluorine, chlorine or bromine) and haloalkyl (for example trifluoromethyl).

A $C_{3-7}$ cycloalkyl group or the cycloalkyl moiety of a $C_{4-8}$ cycloalkylalkyl group may preferably be a cyclobutyl, cyclopropyl or cyclopentyl group but is preferably cyclopropyl or cyclopentyl. A $C_{4-8}$ cycloalkylalkyl group may be cyclopropylmethyl, cyclobutylmethyl, cyclopentylmethyl, cyclohexylmethyl or cycloheptylmethyl but is preferably cyclopropylmethyl or cyclopentylmethyl. The cycloalkyl or cycloalkylalkyl group may be substituted or unsubstituted. Suitable substituents include hydroxy, alkoxy (for example methoxy or ethoxy), halogen (for example fluorine, chlorine or bromine) and haloalkyl (for example trifluoromethyl).

An heteroaryl group or the heteroaryl moiety of an heteroar($C_{1-4}$)alkyl group is preferably phenyl or pyridyl. The heteroaryl moiety may be unsubstituted or substituted for example by a $C_{1-4}$ alkyl group (such as methyl) or an electron-withdrawing substituent such as halogen atom (for example fluorine or chlorine), nitro or trifluoromethyl or an electron-donacting group such as alkoxy or cycloalkoxy. An heteroar($C_{1-4}$) alkyl group is preferably benzyl or substituted benzyl.

The heterocyclic moiety of a heterocyclo($C_{1-4}$)alkyl group may suitably contain one or more heteroatoms, such as oxygen or nitrogen, and conveniently is a morpholinyl group.

Where —NR$_{6a}$R$_{6b}$ together form a 5-membered or 6-membered ring containing an additional heteroatom, the heteroatom is preferably nitrogen or oxygen. The ring formed by —NR$_{6a}$R$_{6b}$ may be unsubstituted or substituted for example by a $C_{1-4}$ alkyl group (such as methyl or ethyl) or a halogen atom (such as fluorine or chlorine) and may contain one or more units of unsaturation. Conveniently —NR$_{6a}$R$_{6b}$ may be a substituted or unsubstituted morpholine or piperazine ring.

In one preferred class of compounds of formula (I), $R_3$ represents a $C_{1-8}$ (preferably $C_{1-5}$) alkyl group, in particular propyl, an ar($C_{1-4}$) alkyl group such as substituted or unsubstituted benzyl or a $C_{3-7}$ cycloalkyl group, in particular cyclopropylmethyl.

In another preferred class of compounds of formula (I), $R_{6a}$ represents a $C_{1-8}$ alkyl group such as methyl or ethyl. $R_{6b}$ conveniently represents a hydrogen atom.

In another preferred class of compounds of formula (I), $R_{6a}$ represents a heteroaryl($C_1$–$C_4$)alkyl group such as 4-pyridylmethyl group.

In another preferred class of compounds of formula (I), $R_8$ represents a hydrogen atom, a $C_{3-7}$ cycloalkyl group, in particular cyclopropyl, or a $C_{1-8}$ alkyl group, in particular iso-propyl.

The term "lower alkyl" is defined for purposes of the present invention as straight or branched chain radicals having from 1 to 5 carbon atoms. Likewise, the term "alkoxy" is defined for purposes of the present invention as RO where R is a straight or branched or cyclic chain radical having from 1 to 6 carbon atoms.

Preferred adenine compounds according to the invention include: 3-Benzyl-6-ethylamino-3H-purine; 6-ethylamino-3-hexyl-3H-purine; 8-cyclopropyl-3-cyclopropylmethyl-6-ethylamino-3H-purine; 6-cyclopentyl-8-cyclopropyl-3-propyl-3H-purine; 3-(3-cyclopentyloxy-4-methoxybenzyl)-6-ethylamino-8-isopropyl-3H-purine; 8-cyclopropyl-3-propyl-6-(4-pyridylmethylamino)-3H-purine; 6-cyclopentylamino-3-(3-cylcopentyloxy-4- methoxybenzyl)-8-isopropyl-3H-purine; 3-(4-chlorobenzyl)-6-ethylamino-8-isopropyl-3H-purine; 3-(4-chlorobenzyl)-6-cyclopentylamino-8-cyclopropyl-3H-purine; 3-(3-cyclopentyloxy-4-methoxybenzyl)-6-ethylamino-3H-purine; 3-benzyl-6-ethylamino-8-(1-methylethyl)-3H-purine; 3-ethyl-6-cyclopentylamino-8-cyclopropyl-3H-purine; 8-cyclopropyl-6-ethylamino-3-(3-methylbutyl)-3H-purine; 3-cyclohexylmethyl-8-cyclopropyl-6-ethylamino-3H-purine; 8-cyclopropyl-3-cyclopropylmethyl-6-ethylamino-3H-purine; 3-ethyl-6-ethylamino-8-((3-cyclopentyloxy-4-methoxy)benzyl)-3H-purine; 3-butyl-8-cyclopropyl-6-ethylamino-3H-purine; 8-cyclopropyl-6-ethylamino-3-propyl-3H-purine; 3-ethyl-6-cyclopentylamino-8-isopropyl-3H-purine; 6-amino-8-cyclopropyl-3-propyl-3H-purine; 8-cyclopropyl-6-cyclopropylamino-3-propyl-3H-purine; 6-cyclopentylamino-8-isopropyl-3-propyl-3H-purine; 6-(3-cyclopentyloxy-4-methoxybenzylamino)-8-cyclopropyl-3-propyl-3H-purine; 6-butylamino-8-cyclopropyl-3-propyl-3H-purine; 3-cyclopropylmethyl-8-isopropyl-6-ethylamino-3H-purine; 8-cyclopropyl-3-ethyl-6-propylamino-3H-purine; 6-cyclohexylamino-8-isopropyl-3-propyl-3H-purine; 3,8-diethyl-6-morpholino-3H-purine; and pharmaceutically acceptable salts thereof.

In certain preferred embodiments, the adenine compound is selected from 3-(3-cyclopentyloxy-4-methoxybenzyl)-6-ethylamino-3H-purine (PDE IV $I_{50}$=2.15 μM); 3-(4-chlorobenzyl)-6-ethylamino-8-isopropyl-3H-purine (PDE IV $I_{50}$=1.13 μM); 3-(3-cyclopentyloxy-4-methoxybenzyl)-6-ethylamino-8-isopropyl-3H-purine (PDE IV $I_{50}$=0.32 μM); and their pharmaceutically acceptable salts.

The present invention is also related to thioisoguanine compounds which are precursors of the adenine compounds described above. In addition to their role as precursor compounds, it has been surprisingly discovered that these compounds also have significant PDE IV inhibitory activity.

The present invention therefore is directed in part to a compound of the formula (II):

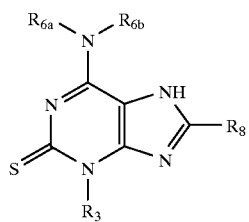

wherein $R_3$, $R_{6a}$, $R_{6b}$ and $R_8$ are the same or different and represent the same groups as those set forth with respect to compound (I) above.

Preferred thioisoguanine compounds according to the present invention include 6-cyclopentylamino-8-cyclopropyl-3,7-dihydro-3-propyl-2H-purin-2-thione (PDE IV $I_{50}$=7.41 μM); 6-cyclopoentylamino-8-cyclopropyl-3,7-dihydro-3-ethyl-2H-purine-2-thione (PDE IV $IC_{50}$=0.19 μM); (particularly preferred) 3-cyclopropyl-3,7-dihydro-3-propyl-6-(4-pyridylmethylamino)-2H-purine-2-thione (PDE IV $I_{50}$=0.41 μM); and their pharmaceutically acceptable salts.

The present invention is also related to 2,6-dithioxanthine compounds which are precursors of the thioisoguanine compounds described above. In addition to their role as precursor compounds, it has been surprisingly discovered that these compounds also have significant PDE IV inhibitory activity.

The present invention therefore is directed in part to a compound of the formula (III)

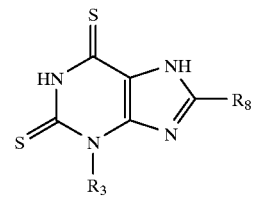

wherein $R_3$ and $R_8$ are the same or different and are represent the same groups as those set forth with respect to compound (I) above.

Preferred dithioxanthine compounds according to the present invention include 3-benzyl-3,7-dihydro-8-(1-methylethyl)-1H-purin-2,6-dithione (PDE IV $I_{50}$=3.40 μM); 3-cyclohexylmethyl-8-cyclopropyl-3,7-dihydro-1H-purine-2,6-dithione (PDE IV $I_{50}$=3.03 μM); 3-(4-chlorobenzyl)-8-isopropyl-3,7-dihydro-2,6-dithio-1H-purin-2,6-dione (PDE IV $I_{50}$=2.40 μM); 8-cyclopropyl-3-cyclopropylmethyl-3,7-dihydro-1H-purine-2,6-dithione (PDE IV $I_{50}$=2.27 μM); 3-(3-cyclopentyloxy-4-methoxybenzyl)-3,7-dihydro-8-isopropyl-1H-purine-2,6-dithione (PDE IV $I_{50}$=0.80 μM); (particularly preferred)8-cyclopropyl-3,7-dihydro-1,3-diethyl-1H-purine-2,6-dithione (PDE IV $I_{50}$=0.42 μM); and their pharmaceutically acceptable salts.

Suitable pharmaceutically acceptable salts are those conventionally known in the art and include, for example, acid addition salts formed with inorganic acids, such as hydrochlorides, phosphates and sulphates and with organic acids such as tartrates, maleates, fumarates and succinates.

The adenine compounds of the present invention, as well as their thioisoguanine and 2,6-dithioxanthine precursors have now been shown to have PDE IV inhibitory activity using standard laboratory tests such as enzyme analysis, the guinea pig tracheal smooth muscle assay and PAF skin oedema and arachidonic acid mouse ear oedema tests and lymphocyte proliferation. These compounds may also find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

Accordingly, the invention is also directed to providing a compound of the invention or a pharmaceutically acceptable salt thereof for use in medicine, in particular for the treatment of conditions where a PDE IV inhibitory effect is indicated (for example chronic obstructive airway disease).

The invention further provides the manufacture of compounds of the invention or pharmaceutically acceptable salts thereof for the manufacture of a medicament for the treatment of conditions whether a PDE IV inhibitory effect is indicated.

In a further aspect, the invention provides a method of treatment of conditions where a bronchodilator or anti-inflammatory agent is indicated comprising administration of a pharmaceutically effective amount of one or more of the compounds of the invention or pharmaceutically acceptable salts thereof.

The active ingredient is preferably presented as a pharmaceutical formulation, conveniently in unit dose form.

According to a further aspect the invention provides a pharmaceutical composition comprising at least one compound of formula (I) or a pharmaceutically acceptable salt thereof formulated for administration by any convenient route. The pharmaceutical compositions of the invention can conveniently be formulated in conventional manner together with one or more pharmaceutically acceptable carriers or excipients.

Compounds according to the invention may conveniently be formulated in dosage forms for oral and parenteral administration, or for administration by inhalation.

For oral administration suitable dosage forms include solid dosage forms such as tablets and capsules which may be prepared by conventional pharmaceutical means with pharmaceutically acceptable excipients such as binders (for example starch or hydroxypropyl methyl cellulose), lubricating agents (such as magnesium stearate or talc), sweetening agents or lubricating agents. Liquid dosage forms which may be used include solutions, syrups or suspensions which may be prepared by conventional means with pharmaceutically acceptable adjuvants such as wetting agents, suspending agents, emulsifying agents and flavoring or perfuming agents.

For parenteral administration the compounds of the invention may conveniently take the form of sterile aqueous or non-aqueous solutions, suspensions or emulsions which may contain stabilizing, suspending or dispersing agents. Compositions may also be in the form of solid compositions such as powders which may be reconstituted with a suitable vehicle such as sterile water or other sterile injectable medium before use.

For administration by inhalation, the active ingredient may be delivered via an aerosol or nebulizer. The active ingredient may be present as a solid, a suspension or a solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Oxol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

The dose of the compounds of the present invention is dependent upon the affliction to be treated, the severity of the symptoms, the route of administration, the frequency of the dosage interval, the presence of any deleterious side-effects, and the particular compound utilized, among other things.

The dose of the active ingredient administered will depend on the particular compound used, the condition of the patient, the frequency and route of administration and the condition to be treated. The compounds of the invention may conveniently be administered one or more times, for example 1 to 4 times per day. A proposed dose of the compounds of the invention is 1 to 10 mg/kg body weight, preferably 100 mg to 1000 mg per day.

According to another aspect of the invention compounds of formula (I) and their pharmaceutically acceptable salts may be prepared by the following methods in which $R_3$, $R_{6a}$, $R_{6b}$ and $R_8$ are as defined for formula (I) unless otherwise indicated.

According to one general process (A) compounds of formula (I) may be prepared by reacting a compound of formula (IV)

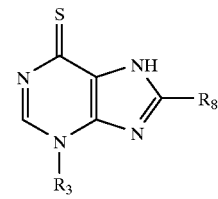

(IV)

with a compound of formula (V):

$R_{6a}R_{6b}NH$ (V)

The reaction of compound (IV) with (V) may conveniently be effected in the presence or absence of a suitable reaction medium and at a temperature of from 0–150° C., preferably at 150° C. Suitable solvents include water, alcohol (for example ethanol) and hydrocarbons (for example benzene).

Compounds of formula (IV) may themselves be prepared by thionation of the corresponding 6-oxo compounds, for example, by treatment with phosphorus pentasulphide in pyridine. The thionation is suitably carried out by treating a suspension of the 6-oxo compound in pyridine with a 20% molar excess of phosphorus pentasulphide.

The corresponding 6-oxo compounds may in turn be prepared from the corresponding 2-thioxanthine derivatives according to methods known in the art (see, for example, Arch Pharm, 244, 11–20 (1906) and J. Org. Chem., 27, 2478–2491 (1962)).

According to another general process (B), compounds of formula (I) may be prepared from compounds of formula (II):

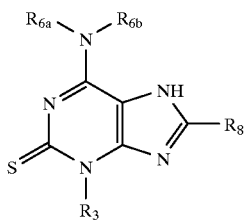

(II)

by reduction using a suitable reducing agent. The reduction may conveniently be effected in the presence of a metal such as Raney nickel. The reduction may conveniently be carried out in a suitable solvent such as an alcohol (for example ethanol), a hydrocarbon (for example benzene) or water and at a suitable temperature. In a particular embodiment, the Raney nickel may be prepared in situ from a nickel/aluminum alloy and a strong base such as sodium hydroxide.

Compounds of formula (II) may themselves be prepared from the corresponding 2,6-dithioxanthine derivatives of formula (III):

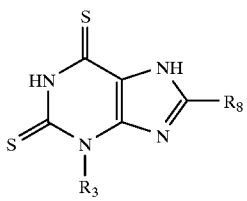

(III)

by reaction with an amine $R_{6a}R_{6b}NH$ according to the method of process (A) above. Compounds of formula (III) in turn may be prepared from the corresponding 2-thioxanthine derivative by thionation, for example, by treatment with phosphorus pentasulphide in pyridine. The 2-thioxanthine compounds are known compounds or may be prepared from readily obtained starting materials by conventional methods.

The following examples illustrate various aspects of the present invention, and are not to be construed to limit the claims in any manner whatsoever.

EXAMPLE 1

3,8-Diethyl-6-morpholino-3H-purine (i) 3,8-Diethyl-hypoxanthine 3,8-diethyl-2-thioxanthine (18.9 g) was dissolved in 370 ml of 2N NaOH Nickel aluminum alloy (75.6 g) (1.4M of Al and 0.6M of Ni) was added in portions over 1.5 hrs at 65° C. After a further 0.5 hr at 65–70° C. the reaction product was filtered, washed with 200 ml of 1N NaOH and the filtrate neutralized with 183 ml of 5N HCl to pH 7. The formed aluminum hydroxide was filtered off, the filtrate concentrated to dryness, the residue suspended in 500 ml of absolute ethanol at 90° C., and the insoluble NaCl filtered off and washed. The filtrate was concentrated to dryness, dissolved in 200 ml of chloroform, filtered and concentrated to dryness again. The residue was crystallized from 150 ml of ethanol to give 3,8-di-ethyl-hypoxanthine (12.68 g) with mp (sublimation at 220° C.) 305–307° C. under decomposition.

(ii) 3,8-Diethyl-6-thiohypoxanthine

The product of stage (i) (8.65 g) and phosphorus pentasulfide (12.0 g) was refluxed in 150 ml of pyridine for 1 hr. Under cooling 59.4 ml of 2N NaOH was added dropwise, the solid filtered off and washed with water. The filtrate was concentrated in vacuo to dryness and the residue suspended in 200 ml of water and collected. The filtrate was extracted three times with 600 ml of chloroform. The residue of the organic phase was combined with the solid collected (total 6.08 g), dissolved in 500 ml of chloroform and filtered through 24 g of silicagel. Fractions 2 and 3 eluted 4.63 g of crude product which was crystallized from 120 ml of methanol to give 3,8-diethyl-6-thiohypoxanthine (3.58 g) with mp (sublimation at 210° C.) 250–270° C. under decomposition. A second crop gave 0.58 g.

Elemental analysis:

| % calc | C 51.90 | H 5.81 | N 26.90 | S 15.40 |
|---|---|---|---|---|
| % found | C 51.76 | H 6.01 | N 26.82 | S 15.64 |

(iii) 3,8-Diethyl-6-morpholino-3H-purine

The product of stage (ii) (52 mg) in 5 ml of morpholine was refluxed for 21 hrs. Evaporation in vacuo gave 65 mg of crude 3,8-diethyl-6-morpholino-3H-purine.

EXAMPLE 2

3,8-Diethyl-6-morpholin-3H-purine (i) 3,8-Diethyl-2,6-dithioxanthine 19.14 g of 3,8-diethyl-2-thioxanthine and 22.75 g of phosphorus pentasulfide were refluxed in 280 ml of pyridine for 4.5 hrs. After cooling to room temperature 113 ml of 2N NaOH were added during 15 minutes under vigorous stirring and cooling. The suspension was filtered, washed with pyridine and concentrated in vacuo. The residue was suspended in 150 ml of water and concentrated to remove the pyridine. Suspension in water and collection of the solid gave the crude product, which is dissolved in 150 ml of 1N NaOH, treated with two portions of 0.5 g of charcoal, and filtered. The filtrate was slowly acidified with 38 ml of 5N HCl to pH 3 and a solid collected. The dried crude product (19.85 g) was suspended in 400 ml of 2-propanol at 95° C. After cooling to room temperature the solid (17.62 g) is collected and washed.

(ii) 3,8-Diethyl-3,7-dihydro-6-morpholino-2H-purine-2-thione

The product of stage (i) (14.42 g) was refluxed in 78.4 ml (900 mmoles) of morpholine for 30 hours. After cooling to room temperature the reaction product was suspended in 100 ml of acetone and the title product (16.49 g) collected and washed.

3,8-diethyl-3,7-dihydro-6-morpholino-2H-purine-2-thione melting point: 295–298° C. (with decomposition).

| Calc. | C 53.22 | H 6.53 | N 23.87 | S 10.93 |
|---|---|---|---|---|
| Found | C 53.01 | H 6.77 | N 23.82 | S 10.97 |

(iii) 3,8-Diethyl-6-morpholino-3H-purine

The product of stage (ii) (7.34 g) was dissolved in 150 ml of 2N NaOH. Ni-Al alloy 50% (22.95 g) (425 mmoles of Al and 196 mmoles of Ni) was added over 1.25 hours at 65° C. added. After another 1.5 hours at 65–70° C. additional 15 ml of 10N NaOH and in portions 11.48 of Ni-Al alloy 50% was added. After another 0.5 hour at 65–70° C. the reaction product was left over night. Dichloromethane (100 ml) was added, the suspension was filtered and the nickel washed with dichloromethane (200 ml) and water (100 ml). The organic phase was separated, washed twice with water and concentrated. The residue was triturated in 50 ml of petroleum-ether to give the title product as a solid (5.40 g) mp 103–107° C.

Elemental analysis:

| % calc  | C 59.75 | H 7.33 | N 26.80 |
|---------|---------|--------|---------|
| % found | C 59.64 | H 7.55 | N 26.35 |

HCl salt crystallized from acetone has mp (sublimation 145° C.) 220–222° C.

EXAMPLE 3

8-Cyclopropyl-3-ethyl-6-ethylamino-3H-purine (i) 8-Cyclopropyl-3-ethyl-6-ethylamino-3,7-dihydro-2H-purine-2-thione 8-cyclopropyl-3-ethyl-2,6-dithioxanthine (20.19 g) prepared according to the method of example 2(i), and 70% ethylamine in water (320 ml 4.0M) were placed in a 450 ml pressure reactor and heated to 150° C. for 6 hours. The reaction solution was cooled to room temperature, treated with 2 portions of charcoal (0.2 g) filtered, and evaporated to dryness. The residue was triturated in methanol (300 ml), concentrated to about 200 ml, and the solid collected (16.48 g), mp 265° with decomposition.

(ii) 8-Cyclopropyl-3-ethyl-6-ethylamino-3H-purine

The product of step (i) (11.85 g) was dissolved in 2N NaOH (270 ml) and 10N NaOH (27 ml) and heated to 65° C. Within 1.25 hours 50% Ni-Al alloy (518 mmoles of Ni and 1125 mmoles of Al) (60.8 g) was added under vigorous stirring at 65–70° C. After a further 0.75 hr at the same temperature the reaction mixture was cooled to room temperature and treated with chloroform (400 ml). The nickel was filtered off and washed with 350 ml of chloroform and 150 ml of water. The filtrate was separated and the chloroform layer evaporated to dryness. The residue (19.64 g) was dissolved in acetone (100 ml), treated with 2 portions of charcoal (0.15 g) filtered, and evaporated. The residue was treated with diethylether (100 ml) and crystals collected (6.10 g), mp 80–96° C. A second crop gave 1.25 g. A recrystallized sample from diisopropylether had mp 103–105° C.

Elemental analysis with 3.3% of water:

| % calc  | C 60.25 | H 7.54 | N 29.28 | O 2.93  |
|---------|---------|--------|---------|---------|
| % found | C 60.52 | H 7.46 | N 29.10 | O 2.92* |

*(by difference)

HCl salt crystallized from methanol-acetone with mp 183–191° C.

EXAMPLE 4

A. 8-(3-cyclopentyloxy-4-methoxybenzyl)-3-ethyl-6-ethylamino-3H-purine hydrochloride B. 8-(3-cyclopentyloxy-4-hydroxybenzyl)-3-ethyl-6-ethylamino-3H-purine (i) 3-Cyclopentyloxy-4-methoxy-benzyl alcohol To a solution of 48.70 g (220 mmoles) of 3-cyclopentyloxy-4-methoxybenzaldehyde in 250 ml of methanol was added portionwise 8.57 g (220 mmoles) of 97% sodium borohydride within 10 min at 15–22° C. under cooling. After a further 20 min the methanol was removed in vacuo and the residue taken up in 10 ml of water and 300 ml of ether. The ether phase was evaporated to dryness: 48.5 g (99.2%) of liquid benzyl alcohol.

(ii) 3-Cyclopentyloxy-4-methoxy-benzyl cyanide

To a solution of 40.00 g (180 mmoles) of benzyl alcohol in 530 ml of dichloromethane was added within 5 min 32.7 ml (450 mmoles) of thionyl chloride. The solution was evaporated in vacuo to dryness, which was repeated after toluene addition: 46.30 g (106.9%) of crude benzyl chloride, which was dissolved in 230 ml of dimethylformamide and treated with 23.50 g (360 mmoles) of potassium cyanide. The mixture was heated for 4 hours to 50–55° C. The salt was filtered off and the filtrate evaporated in vacuo to dryness, which was repeated after the addition of water, the residue was taken up in ether and extracted with 1N NaOH. The ether phase is evaporated to dryness to yield 41.20 g (99.0%) of crude benzyl cyanide.

(iii) (3-Cyclopentyloxy-4-methoxyphenyl)acetyl chloride 42.02 g (180 mmoles) of benzyl cyanide were refluxed in 410 ml of 94% ethanol, 106 ml of water, and 180 ml of 10N NaOH for 20 hours. The ethanol was removed in vacuo, the solution diluted to 800 ml with water, treated twice with 2 g of charcoal, filtered, and acidified with 185 ml of 10N HCl. The acid crystallized slowly, was collected and dried at 30° C.: 42.2 g (92.9%) of acid. 1.51 g (2.3%) could be extracted by ether from the filtrate. Both parts (173 mmoles) are combined and refluxed in 500 ml of dichloromethane and 31.4 ml (433 mmoles) of thionyl chloride for 1.5 hours. The solution was treated twice with 2 g of charcoal, filtered and evaporated to dryness. This was repeated twice with little toluene: 48.70 g (>100%) of crude acetyl chloride as a reddish liquid.

(iv) 8-(3-Cyclopentyloxy-4-methoxybenzyl)-3-ethyl-2-thioxanthine 10.02 g (45 mmoles) of 5,6-diamino-1-ethyl-2-thiouracil hydrochloride was dissolved in 200 ml of pyridine, treated with 6.05 g (57 mmoles) of sodium carbonate and 15.5 g (56 mmoles) of Example 4 (iii) dissolved in 25 ml of ether added within 10 minutes at 5–10° C. After 1.5 hours at room temperature the solid was filtered off and the filtrate evaporated in vacuo to dryness. The residue was dissolved in 100 ml of 2N NaOH and 200 ml of water and brought to reflux, within 1 hour 70 ml are distilled off. The solution was filtered and neutralized to pH 7.5 with 52 ml of 5N HCl. The solid was collected and dried: 14.37 g (79.7%) of crude 2-thioxanthine (from the water 4.2 g of the phenyl acetic acid was recovered), which was suspended in 250 ml of hot methanol and collected again: 10.68 g (59.3%) of purified 2-thioxanthine, which was dissolved is 100 ml of 1N NaOH and filtered. The filtrate was acidified to pH 6 and the solid collected: 8.82 g (48.9%) of 2-thioxanthine with mp (260° C.) 280–310° C. under decomposition.

(v) 8-(3-Cyclopentyloxy-4-methoxybenzyl)-3-ethyl-2,6-dithioxanthine 8.41 g (21 mmoles) of 2-thioxanthine are refluxed with 5.60 g (25.2 mmoles) of phosphorus pentasulfide in 80 ml of pyridine. After 5.5 hours 27.7 ml (55.4 mmoles) of 2N NaOH were added at 5–10° C. The solid was filtered off and washed with pyridine. The filtrate was evaporated in vacuo to dryness, the residue is suspended in 200 ml of water with little tetrahydrofuran (THF) for crystallization, the suspension is concentrated and the solid at pH 8 collected and washed. Redissolution in 100 ml of 0.5 N NaOH, treatment with charcoal (20%), filtration and acidification to pH 6 yielded the solid crude dithioxanthine 7.84 g (89.6%). Crystallization from chloroform and suspension in hot methanol gave 5.31 g (60.7%) of dithioxanthine with mp 241–3° C. The mother liquors were combined (2.36 g) and filtered with chloroform through 60 g of silicagel in a column: 1.73 g (19.8%) were isolated as a second crop.

(vi) 8-(3-Cyclopentyloxy-4-methoxy-benzyl)-3-ethyl-6-ethylamino-3,7-dihydro-2H-purine-2-thione 6.67 g (16 mmoles) of dithioxanthine and 52 ml of 70% ethylamine in water were heated to 150° C. in a pressure reactor (250 psi) for 12 hours under nitrogen. The solution was treated with charcoal (5%), filtered, and evaporated in vacuo to dryness. The residue was suspended in water, acidified with 1N HCl to pH 4 and neutralized to pH 8 with sodium bicarbonate. The solid was collected, washed and dried to give 6.66 g (97.4%) of crude thioisoguanine.

(vii) A. 8-(3-Cyclopentyloxy-4-methoxy-benzyl)-3-ethyl-6-ethylamino-3H-purine hydrochloride and B. 8-(3-cyclopentyloxy-4-hydroxy-benzyl)-3-ethyl-6-ethylamino-3H-purine hydrochloride 6.41 g (15 mmoles) of crude thioisoguanine and 9.70 g (165 mmoles) of neutral Raney-nickel were refluxed in 70 ml of 1-propanol for 3 hours. The nickel was filtered off and the filtrate evaporated in vacuo to dryness. The residue (5.86 g/98.8%) was dissolved in chloroform and extracted extensively with 1N NaOH. The NaOH solution was acidified with 5N HCl to pH 4 and neutralized with sodium bicarbonate to pH 7.5. An oil precipitated, which crystallized slowly and the solid collected: 0.49 g of 8-(3-cyclopentyloxy-4-hydroxy-benzyl)-3-ethyl-6-ethylamino-3H-purine with mp 172–4° C. The chloroform solution was evaporated to dryness: 3.76 g (63.4%) of crude 3H-purine, which was dissolved in 30 ml of methanol and treated with 10 ml of 1N methanolic HCl. The solution was evaporated in vacuo to dryness and the residue crystallized from acetone-ethyl acetate: 3.66 g (56.5%) of 8-(cyclopentyloxy-4-methoxybenzyl)-3-ethyl-6-ethylamino-3H-purine hydrochloride with mp 169–71° C.

Elemental analysis for $C_{22}H_{30}ClN_5O_2$

|       |         |        |         |
|-------|---------|--------|---------|
| Calc. | C 61.17 | H 7.00 | N 16.21 |
| Found | C 61.09 | H 6.77 | N 16.18 |

EXAMPLE 5

3-(3-cyclopentyloxy-4-methoxybenzyl)-6-ethylamino-8-isopropyl-3H-purine hydrochloride (i) 3-Cyclopentyloxy-4-methoxy-benzaldehyde 77.70 g (500 mmoles) of isovanillin and 69.40 g (600 mmoles) of 97% potassium t-butoxide (t-BuOK) dissolved in 800 ml of 1-propanol, 69.0 ml 630 mmoles), and the solution refluxed. After 3 hours another 9.25 g (80 mmoles) of t-BuOK were added at 80° C. and the suspension refluxed for another 3 hours. The solid was filtered off and the filtrate evaporated in vacuo to dryness. The residue was dissolved in ether and extracted with 1N NaOH. The ether phase was evaporated to dryness: 85.40 g (77.5%) of cyclopentyloxy-benzaldehyde was isolated.

(ii) 3-Cyclopentyloxy-4-methoxy-benzaldehyde-oxime 85.4 g (388 mmoles) of 3-cyclopentyloxy-4-methoxybenzaldehyde were dissolved in 350 ml of 94% ethanol and added within 10 minutes at 15–20° C. to a solution of 29.7 g (427 mmoles) of hydroxylammonium chloride and 52.8 g (388 mmoles) of sodium acetate trihydrate (3 $H_2O$) in 230 ml of water. After 2 hours the ethanol was removed in vacuo, the residue treated with 16.3 g (194 mmoles) of sodium bicarbonate until $CO_2$ formation ceased and extracted with ether. Evaporation of the ether phase gave 91.0 g (99.7%) of oxime as a mixture of the 2 isomers.

(iii) 3-Cyclopentyloxy-4-methoxy-benzylamine 73.5 g (320 mmoles) of oxime, 80 ml of methanol, 55 g of liquid ammonia, and 18.5 g of neutral Raney-nickel are placed into a 450 ml pressure reactor. Hydrogen gas was added up to a pressure of 1,200 psi and the whole heated to 75–80° C., when the pressure dropped to 600 psi hydrogen gas was added again to 1,200 psi. After 4 hours the pressure reached 1080 psi and remained constant. The nickel was filtered off and washed with methanol. The filtrate is evaporated to dryness, dissolved in ether and extracted with 1N NaOH. The ether phase was evaporated to dryness: 68.9 g (97.3%) of benzylamine.

(iv) 3-Cyclopentyloxy-4-methoxy-benzyl-isothiocyanate 82.3 g (372 mmoles) of benzylamine were dissolved in 10 ml of toluene and added at 15–20° C. (with cooling) within 20 minutes to an emulsion of 22.5 ml (372 mmoles) of carbon disulfide and 14.88 g (372) mmoles) of NaOH in 52 ml of water. The reaction mixture was heated to 75–80° C. for 1 hour and cooled to 40° C. Within 15 minutes, 35.4 ml (372 mmoles) of ethyl chloroformate were added at 40–45° C. The emulsion was brought to about pH 8 with 2N NaOH and heated to 55–60° C., gas formation ceased after about 10 hours keeping the pH at 8 with 2N NaOH (total about 8 ml). The organic layer was collected and the solvent evaporated: 96.3 g (98.3%) of benzyl isothiocyanate.

(v) 1-(3-Cyclopentyloxy-4-methoxy-benzyl)-2-thiourea 96.3 g (366 mmoles) of benzylisothiocyanate were dissolved in 100 ml of THF and treated with 44.2 ml (732 mmoles) of 32% ammonia solution. After 0.5 hour at 40–45° C., 300 ml of water were added and the THF removed in vacuo. The gummy suspension is treated with 200 ml of ether, the crystals collected and washed with water and ether. Suspension in 30 ml of methylenechloride and collection gave 65.77 g (64.2%) of benzyl-2-thiourea with mp 144–5° C.

(vi) 6-Amino-1-(3-cyclopentyloxy-4-methoxy-benzyl-2-thiouracil 29.65 g (256 mmoles) of 97% t-BuOK were dissolved in 240 ml of 2-propanol. 65.33 g (233 mmoles) of 2-thiourea and 25.3 ml (238 mmoles) of ethyl cyanoacetate were added at 80° C. After 30 minutes at reflux a solution was formed and after 4.5 hours an additional 2.96 g (25.6 mmoles) of t-BuOK and 4.97 ml (46.6 mmoles) of ethyl cyanoacetate added. After 22 hours of refluxing the solid was collected, combined with the residue of the filtrate, dissolved in 1 l of water and precipitated with about 50 ml of 5N HCl (pH 3–4). The solid is collected, washed, dried, recrystallized by suspension in 1 l of refluxing acetone, concentrated to about 300 ml and collected at 23° C.: 80.65 g (85.7%) of uracil containing 1 equivalent of acetone, mp 225–7° C.

(vii) 6-Amino-1-(3-cyclopentyloxy-4-methoxy-benzyl)-5-nitroso-2-thiouracil 68.9 g (170 mmoles) of uracil are dissolved in 650 ml of acetic acid, for removal of acetone 100 ml are distilled off in vacuo, and at 65–70° C. 43.4 ml (174 mmoles) of 4N sodium nitrite solution were added within 10 minutes. After further 5 minutes the suspension was cooled to 30° C. and diluted with 1.7 l of water. The solid was collected, washed, and dried: 64.08 g (100%) of nitrosouracil, which was dissolved in 330 ml of 1N NaOH and 300 ml of water, filtered, and acidified with 5N HCl to pH 2, to keep it in suspension 2 l of water were added. The solid was collected and washed, suspended in 60 ml of methanol and collected again: 54.2 g (84.7%) of nitrosouracil.

(viii) 1-(3-cyclopentyloxy-4-methoxy-benzyl)-5,6-diamino-2-thiouracil 15.06 g (40 mmoles) of nitrosouracil are suspended in 300 ml of THF and hydrogenated with hydrogen gas and 6 g of neutral Raney-nickel for 2.5 hours, when hydrogen uptake ceased. After 1 hour all was dissolved and thereafter a new precipitate formed, which is dissolved in a mixture of methylenechloride and methanol. The nickel was filtered off and the filtrate evaporated in vacuo to dryness: 13.96 g (96.3%) of crude diaminouracil.

(ix) 6-Amino-1-(3-cyclopentyloxy-4-methoxy-benzyl)-5-isobutylamino-2-thiouracil

A two phase solution of 15.01 g (41.4 mmoles) of diaminouracil, 180 ml of THF, 150 ml of water, 6.96 g (82.8 mmoles) of sodium bicarbonate, and 10.52 ml (62.1 mmoles) of isobutyric anhydride is heated to 55° C. under nitrogen for 1 hour. The THF was evaporated in vacuo and the residue diluted with 200 ml of water (pH 8). The solid was collected, washed, and dried: 16.25 g (90.7%) of isobutyrylaminouracil.

(x) 3-(3-Cyclopentyloxy-4-methoxy-benzyl)-8-isopropyl-2-thioxanthine 17.81 g (41.2 mmoles) of isobutyrylaminouracil were refluxed for 0.75 hour in 120 ml of 1N NaOH and 80 ml of water. The solution was treated twice with 0.5 g of charcoal, filtered, acidified with 5N HCl, and put to pH 7–8 with sodium bicarbonate solution. The solid was collected, washed, and dried: 15.31 g (89.6%) of 2-thioxanthine with mp 270–6° C. (with decomposition).

(xi) 3-(3-Cyclopentyloxy-4-methoxybenzyl)-8-isopropyl-2,6-dithioxanthine 15.17 g (36.6 mmoles) of 2-thioxanthine and 9.76 g (43.9 mmoles) of phosphorus pentasulfide were refluxed under nitrogen in 140 ml of pyridine for 5.5 hours. At 5–10° C. 48.3 ml (96.6 mmoles) of 2N NaOH were added dropwise. The solid was filtered of and washed with pyridine. The filtrate was evaporated in vacuo to dryness and treated with 300 ml of water. The suspension was adjusted to pH 7 with sodium bicarbonate solution and the solid collected, washed, dissolved in 200 ml of 0.5N NaOH solution, treated twice with 1.6 g of charcoal, filtered, acidified with 5N HCl and neutralized with sodium bicarbonate solution to pH 7. The solid was collected, washed, and dried: 14.64 g (92.9%) of crude dithioxanthine, which was dissolved in 400 ml of methylenechloride and filtered through 60 g of silicagel in a column. The solvent was evaporated and the residue suspended in 20 ml of 100% ethanol and collected: 14.34 g (82.2%) of dithioxanthine with mp 204–6° C. (containing 1 mol EtOH).

(xii) 3-(3-Cyclopentyloxy-4-methoxy-benzyl)-3,7-dihydro-6-ethylamino-2H-purine-2-thione 6.20 g (13 mmoles) of dithioxanthine and 42 ml of 70% ethylamine in water were placed into a 450 ml pressure reactor and heated to 150° C. (240 psi) for 12 hours. The solution was filtered and evaporated to dryness. The residue was suspended in water, acidified with 1N HCl to pH 3, and neutralized with sodium bicarbonate solution to pH 7–8. The solid was collected, washed, and dried: 5.48 g (95.5%) of thioisoguanine with mp 72–7° C.

(xiii) 3-(3-Cyclopentyloxy-4-methoxybenzyl)-6-ethylamino-8-isopropyl-3H-purine hydrochloride 5.43 g (12.3 mmoles) of thioisoguanine and 7.9 g of neutral Raney-nickel were refluxed in 60 ml of 1-propanol for 4.5 hours. The nickel was filtered off and the filtrate evaporated in vacuo to dryness: 4.90 g (97.2%) of crude purine, which was dissolved in 20 ml of chloroform, extracted with 1N NaOH and filtered through 30 g of silicagel in a column. The solvent was evaporated, the residue dissolved in 25 ml of methanol, treated with 11 ml of methanolic 1N HCl solution and evaporated to dryness. The residue was suspended in 80 ml of ethyl acetate and collected: 3.49 g (63.6%) of 3H-purine hydrochloride with mp 202–12° C.

Elemental analysis for $C_{23}H_{32}ClN_5O_2$

| Calc. | C 61.94 | H 7.23 | N 15.70 | O 7.17 |
| Found | C 62.17 | H 7.02 | N 15.66 | O 7.30 |

EXAMPLE 6

3-(3-Cyclopentyloxy-4-methoxybenzyl)-6-ethylamino-3H-purine hydrochloride (i) 3-(3-Cyclopentyloxy-4-methoxy-benzyl)-2-thioxanthine 14.62 g (40 mmoles) of 1-(3-cyclopentyloxy-4-methoxy-benzyl)-5,6-diamino-2-thiouracil were dissolved in 200 ml of formic acid. The solution was concentrated in vacuo at room temperature to remove the water. 50 ml of formic acid were added and the procedure repeated. After a total of 1 hour the formic acid solution was concentrated to 30 ml at 25° and diluted with 300 ml of water. The crystals were collected, washed, and dried: 13.48 g (86.3%) of crude 5-formamide (mp 210–30° C.), which was refluxed in 86 ml of 1N NaOH for 15 min. The turbid solution was treated twice with 0.6 g of charcoal, filtered, acidified with 5N HCl to pH 2, and neutralized to pH 6.5. The amorphous solid was collected, washed, and dried at 60° C.: 11.93 g (80.1%) of crude 2-thioxanthine, which was dissolved in 150 ml of THF, treated with charcoal (5%), filtered, concentrated to 40 ml, and diluted with 250 ml of ethanol. After concentration to 120 ml the formed solid is collected, washed, and dried: 9.21 g (61.9%) of 2-thioxanthine with mp 254–65° C.

Elemental analysis for $C_{18}H_{20}N_4O_3S$

| Calc. | C 58.05 | H 5.41 | N 15.04 | O 12.89 |
| Found | C 58.13 | H 5.41 | N 14.93 | O 13.11 |

(ii) 3-(3-Cyclopentyloxy-4-methoxy-benzyl)-2,6-dithioxanthine 8.94 g (24 mmoles) of 2-thioxanthine and 6.40 g (28.8 mmoles) of phosphorus pentasulfide were refluxed in 96 ml of pyridine under nitrogen for 1.5 hours. At 5–10° C. 31.7 ml (63.4 mmoles) of 2N NaOH were added under cooling and the mixture diluted with 30 ml of pyridine. The solid was filtered off and the filtrate evaporated in vacuo to dryness. The residue was suspended in 30 ml of water and the solid collected, dissolved in 160 ml of 0.5N NaOH, filtered, treated with charcoal (20%), filtered again, acidified with 5N HCl to pH 5, the solid collected, washed, and dried: 9.03 g (96.9%) of crude dithioxanthine. The product was dissolved in 400 ml of chloroform and filtered through 30 g of silicagel in a column. The solvent was removed in vacuo, the residue dissolved in 50 ml of THF, filtered, concentrated to 30 ml, diluted with 200 ml of ethanol, concentrated again to 150 ml and the solid collected, washed, and dried: 8.65 g (92.8%) of dithioxanthine with mp 215–8° C.

Elemental analysis for $C_{18}H_{20}N_4O_2S_2$ with 0.25M of ethanol and 0.5M of water

| | | | | |
|---|---|---|---|---|
| Calc. | C 54.32 | H 5.54 | N 13.70 | O 10.76 |
| Found | C 54.67 | H 5.32 | N 13.80 | O 10.20 |

(iii) 3-(3-Cyclopentyloxy-4-methoxy-benzyl)-3,7-dihydro-6-ethylamino-2H-purine-2-thione 4.66 g (12 mmoles) of dithioxanthine and 48.3 ml (60 mmoles) of 70% ethylamine in water were heated to 150° C. in a 450 ml pressure reactor under $N_2$ for 12 hours (240 psi). The solution was treated with charcoal (5%), filtered and evaporated to dryness. The residue was taken up in 100 ml of water, acidified with 1N HCl to pH 3 and neutralized with sodium bicarbonate to pH 7, and the solid collected: 4.43 g (92.5%) of crude thioisoguanine with mp 99–103° C.

(iv) 3-(Cyclopentyloxy-4-methoxy-benzyl)-6-ethylamino-3H-purine hydrochloride 4.39 g (11 mmoles) of thioisoguanine and 7.10 g (121 mmoles) of neutral Raney-nickel are refluxed in 50 ml of 1-propanol for 4.5 hours. The nickel was filtered off and the filtrate evaporated to dryress. The residue (3.79 g/93.8%) was dissolved in 20 ml of chloroform and 0.4 ml methanol and filtered through 24 g of silicagel in a column also with 2% methanol. The combined fractions were washed with 1N NaOH and the organic phase evaporated to dryness. The residue (2.69 g/66.6%) was dissolved in 30 ml of dichloromethane and 0.6 ml methanol and again filtered through 30 g of silicagel. A total of 1.86 g (46.0%) of 3H-purine was isolated, which was dissolved in 20 ml of methanol, treated with 5.4 ml of 1N methanolic HCl, and evaporated in vacuo to dryness. Crystallization and recrystallization from dichloromethane and ethyl acetate gave 1.75 g (39.4%) of 3H-purine hydrochloride with mp 170–85° C.

Elemental analysis for $C_{20}H_{26}C_1N_5O_2$

| | | | | |
|---|---|---|---|---|
| Calc. | C 59.47 | H 6.49 | N 17.34 | O 7.92 |
| Found | C 59.72 | H 6.44 | N 17.25 | O 8.24 |

EXAMPLE 7

8-Cyclopropyl-6-(4-pyridylmethylamino)-3-propyl-3H-purine dihydrochloride (i) 8-Cyclopropyl-3-propyl-2,6-dithioxanthine In a 5 L 3-necked flask fitted with a mechanical stirrer and a condenser with a drying tube were placed 2.2 L of pyridine and 8-cyclopropyl-3-propyl-2-thio-6-oxo-xanthine (220 g, 0.88 mol). Phosphorus pentasulfide (236 g, 1.06 mol) was added and the mixture was heated under reflux for 5 hours and stored overnight at room temperature. The reaction mixture was cooled to 5–10° and 3 N aqueous sodium hydroxide (770 ml) was added over 1.5 hours with stirring. Stirring was continued for 30 minutes after removal of the cooling bath and the precipitated product was collected by suction filtration. The filter cake was washed successively with pyridine (300 ml) and four 300 ml portions of tetrahydrofuran. The solvents are evaporated in vacuo and the solid residue was stirred with water (750 ml), filtered and washed with water. The crude product was dissolved in 1.7 L of 1 N sodium hydroxide and stirred with 15 g of Darco G-60. The charcoal was filtered and the treatment was repeated with a fresh portion of charcoal. The solution was acidified to pH 1.5 with 6 N hydrochloric acid and the pale yellow precipitate was collected. The solid was dissolved again in 1.7 L of 1N sodium hydroxide and treated successively with two portions of charcoal as above. The solution was acidified and the precipitate was collected and washed with water. After drying to constant weight at 54° C. under vacuum, there was obtained 128 g (56%) of the title compound, mp over 245° C.

(ii) 8-Cyclopropyl-3,7-dihydro-3-propyl-6-(4-pyridylmethylamino)-2H-purine-2-thione 5.33 g (20 mmoles) of 8-cyclopropyl-3-n-propyl-2,6-dithioxanthine and 21.3 ml (200 mmoles) of 95% 4-picolylamine were heated under argon to 150–5° C. After 14 hours the cooled solution was poured into 100 ml of water, acidified with 19 ml of 10N HCl and 1N HCl to pH 6, where an orange colored gum was formed. With sodium bicarbonate the mixture was neutralized to pH 7. With time the gum crystallized and the solid is collected and washed. The residue was suspended in acetone and the crystals collected: 3.92 (57.6%) of crude product. The filtrate was evaporated to dryness, dissolved in 40 ml of 0.5N NaOH, extracted 4 times with methylenechloride, and acidified again with 5N HCl to pH 6. Again the gum crystallized over 48 hours and the mixture was neutralized to pH 7 with bicarbonate and the solid collected: 1.75 g (25.7%) of crude product. Both parts were dissolved in 30 ml of methylenechloride and filtered through 30 g of silicagel in a column. 150 mg (2.8%) of starting material was recovered first, then 5.04 g (74.0%) of product was recovered with 5% of methanol, which was dissolved in 32 ml of 1N HCl, treated with 250 mg of charcoal, filtered, and neutralized with 7.5 ml of 2N NaOH and sodium bicarbonate solution to pH 7–8. The water phase was decanted from the gum and the latter washed with water and crystallized from acetone: 4.08 g (59.9%) of thioisoguanine with mp 204–210° C. with decomposition.

(iii) 8-Cyclopropyl-6-(4-pyridylmethylamino)-3-propyl-3H-purine dihydrochloride 3.06 g (9 mmoles) of thioisoguanine and 5.8 g of neutral Raney-nickel were refluxed under argon in 1-propanol for 4 hours. The nickel was filtered off and washed with methanol. The filtrate as evaporated to dryness, the residue dissolved in 20 ml of methylenechloride, the solution extracted with 1 N NaOH, and evaporated to dryness: 2.43 g (87.4%) of crude purine, which was dissolved in 20 ml of methanol, treated with 17 ml of 1N methanolic HCl and evaporated again to dryness. Crystallization from isopropanol gives 1.09 g (36.3%) of purine dihydrochloride with mp 157–65° C.

EXAMPLE 8

6-Cyclopentylamino-8-cyclopropyl-3-propyl-3H-purine hydrochloride (i) 6-Cyclopentylamino-8-cyclopropyl-3,7-dihydro-3-propyl-2H-purine-2-thione 5.33 g (20 mmoles) of 8-cyclopropyl-3-n-propyl-2,6-dithioxantine and 42 ml of cyclopentylamine were heated in a 450 ml pressure reactor to 150° C. (50 psi) with the exclusion of air. After 20 hours the solution was transferred with methanol to a round bottom flask and evaporated in vacuo to dryness. The residue was crystallized from acetone: 1.07 g (15.1) of thioisoguanine hydrochloride with mp 196–98° C. The mother liquor was dissolved in methylenechloride, extracted with sodium bicarbonate solution and filtered through 45 g of silicagel on a column. The first unpolar 0.54 g were discarded and the rest gave 4.63 g (72.9%) of the crude thioisoguanine as a gum.

Elemental analysis for 6-cyclopentylamino-8-cyclopropyl-3,7-dihydro-3-propyl-2-thio-2H-purin-2-one hydrochloride

| Calc. | C 54.30 | H 6.84 | N 19.79 |
|---|---|---|---|
| Found | C 54.42 | H 6.73 | N 19.57 |

(ii) 6-Cyclopentylamino-8-cyclopropyl-3-n-propyl-3H-purine hydrochloride 4.49 g (14.1 mmoles) of thioisoguanine and 9.2 g of neutral Raney-nickel were refluxed in 45 ml of 1-propanol for 5 hours. The nickel was filtered off and the filtrate evaporated to dryness. The residue (>100%) was dissolved in 30 ml of methanol, treated with 16.9 ml of 1N methanolic HCl solution, and evaporated to dryness. The residue was dissolved in methylenechloride, treated with 0.12 g of charcoal, filtered, concentrated, diluted with acetone and the remaining methylene chloride removed by distillation. The crystals were collected: 1.04 g (22.9%) of purine hydrochloride with mp 218–221° C., a second crop gave 0.61 g (13.4%).

Elemental analysis for $C_{16}H_{24}ClN_5$

M.W. 321.86 89%+11% $CH_2Cl_2$

| Calc. | C 59.71 | H 7.52 | N 21.76 | Cl 11.01 |
|---|---|---|---|---|
| Found | C 59.82 | H 7.40 | N 21.76 | Cl 19.40 (diff) |

EXAMPLE 9

THIOISOGUANINE DERIVATIVES

Following the previously set forth methods, the following thioisoguanine derivatives of the present invention were synthesized. The chemical name and melting point are provided in Table 1 below.

TABLE 1

THIOISOGUANINES

| Compound | m.p. (°C.) |
|---|---|
| 3,8-diethyl-3,7-dihydro-6-morpholino-2H-2-thio-purin-2-one | 295–298(dec) |
| 3-(cyclopropylmethyl)-3,7-dihydro-8-isopropyl-(1-methyl)-6-propylamino-2-thio-2H-purin-2-one | 208–210 |
| 3,7-dihydro-6-ethylamino-3-hexyl-2-thio-2H-purin-2-one | 235–237 |
| 3,7-Dihydro-3-hexyl-6-methylamino-2-thio-2H-purin-2-one | 217–219 |

TABLE 1-continued

THIOISOGUANINES

| Compound | m.p. (°C.) |
|---|---|
| 3-benzyl-3,7-dihydro-6-methylamino-2-thio-2H-purin-2-one | 253–255 |
| 8-cyclopropyl-3,7-dihydro-6-ethylamino-3-(3-methylbutyl)-2-thio-2H-purin-2-one | 250–254 |
| 8-cyclopropyl-3,7-dihydro-3-ethyl-6-propylamino-2-thio-2H-purin-2-one | 270–272 |
| 3-butyl-3,7-dihydro-6-ethylamino-2-thio-2H-purin-2-one | (220) 246–248 |
| 3-butyl-8-cyclopropyl-3,7-dihydro-6-ethylamino-2-thio-2H-purin-2-one | 226–228 |
| 6-ethylamino-3,7-dihydro-3-propyl-2-thio-2H-purin-2-one | 247–251 |
| 8-cyclopropyl-6-ethylamino-3,7-dihydro-3-propyl-2-thio-2H-purin-2-one | 238–239 |
| 8-cyclopropyl-3-cyclopropylmethyl-6-ethylamino-3,7-dihydro-2-thio-2H-purin-2-one | 247–249 |
| 3-benzyl-6-ethylamino-3,7-dihydro-2-thio-2H-purin-2-one | 254–257 |
| 8-cyclopropyl-6-cyclopropylamino-3-propyl-3,7-dihydro-2-thio-2H-purin-2-one hydrochloride | 208–226 dec |
| 3-((2-methyl)butyl))-6-(2-(piperazine-1-yl)ethylamino)-3,7-dihydro-2-thio-2H-purin-2-one | |
| 3-cyclohexylmethyl-3,7-dihydro-6-ethylamino-2-thio-2H-purin-2-one | 295–300 |
| 3-benzyl-6-ethylamino-3,7-dihydro-8-(1-methylethyl)-2-thio-2H-purin-2-one | |
| 3-cyclohexylmethyl-8-cyclopropyl-3,7-dihydro-6-ethylamino-2-thio-2H-purin-2-one | 278–282 |
| 6-benzylamino-8-(cyclopropyl)-3,7-dihydro-3-(propyl)-2-thio-2H-purin-2-one hydrochloride | 180–185 |
| 8-(cyclopropyl)-3,7-dihydro-6-hexylamino-3-(propyl)-2-thio-2H-purin-2-one hydrochloride | 170–190 |
| 6-butylamino-8-cyclopropyl-3,7-dihydro-3-propyl-2-thio-2H-purine-2-one | 231–233 |
| 6-cyclopropyl-3,7-dihydro-6-(2-hydroxyethylamino)-2-thio-2H-purine-2-one | 188–192 |
| 6-amino-8-cyclopropyl-3,7-dihydro-3-propyl-2-thio-2H-purine-2-one | 220–265 |
| 6-cyclopentylamino-3-ethyl-3,7-dihydro-8-isopropyl-2-thio-2H-purine-2-one | 301–304 |
| 6-cyclohexylamino-3,7-dihydro-8-isopropyl-3-propyl-2-thio-2H-purine-2-one | 303 dec |
| 6-cyclopentylamino-3,7-dihydro-8-isopropyl-3-propyl-2-thio-2H-purine-2-one | 295 dec |
| 6-cyclopentylamino-3-ethyl-8-cyclopropyl-3,7-dihydro-2-thio-2H-purine-2-one | 245 dec |
| 3-(4-chlorobenzyl)-6-cyclopentylamino-3,7-dihydro-8-isopropyl-2-thio-2H-purine-2-one | 244–248 |
| 6-cyclopentylamino-3-(3-cyclopentyl-4-methoxybenzyl)-3,7-dihydro-8-isopropyl-2-thio-2H-purine-2-one | 230–235 |
| 3-(2-chlorobenzyl)-6-cyclopentylamino-3,7-dihydro-8-isopropyl-2-thio-purine-2-one | |
| 8-cyclopropyl-3,7-dihydro-6-(3-pentyl)-3-propyl-2-thio-2H-purin-2-one | 220 dec |
| 6-ethyl-8-isopropyl-3,7-dihydro-3-(4-pyridylmethyl)-2-thio-2H-purin-2-one | 238–40 |

EXAMPLE 10

ELEMENTAL ANALYSIS OF THIOISOGUANINE DERIVATIVES

A. Elemental analysis for 6-butylamino-8-cyclopropyl-3,7-dihydro-3-propyl-2H-purine-2-thione:

| Calc.  | C 58.98 | H 7.59 | N 22.93 |
|--------|---------|--------|---------|
| Found  | C 58.99 | H 7.52 | N 22.92 |

B. 3-(cyclopropylmethyl)-3,7-dihydro-8-isopropyl-6-propylamino-2H-purine-2-thione Melting point: 208–210° C.
Elemental analysis:

| Calc.  | C 62.26 | H 8.01 | N 24.20 |
|--------|---------|--------|---------|
| Found  | C 62.34 | H 8.06 | N 23.89 |

C. Elemental analysis for 3-cyclopropylmethyl-8-isopropyl-6-ethylamino-3H-purine:

| Calc.  | C 64.84 | H 8.16 | N 27.00 |
|--------|---------|--------|---------|
| Found  | C 64.42 | H 7.86 | N 26.87 |

D. Elemental analysis for 6-benzylamino-3-ethyl-8-isopropyl-6-ethylamino-3H-purine:

| Calc.  | C 69.12 | H 7.17 | N 23.71 |
|--------|---------|--------|---------|
| Found  | C 69.27 | H 7.44 | N 23.60 |

EXAMPLE 11

PDE IV INHIBITION BY THIOISOGUANINE COMPOUNDS

The PDE IV inhibitory activity of certain of the foregoing thioisoguanine compounds was determined according to the procedures set forth below. The results are provided in Table 2.

Type IV Phosphodiesterase Enzyme Isolation Protocol

The Type IV PDE is isolated from bovine tracheal smooth muscle using a procedure similar to that previously described by Silver, P. J., Hamel, L. T., Perrone, M. H. Bentley, R. G. Bushover, C. R., Evans, D. B.: Eur. J. Pharmacol. 50:85,1988.(1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity

Enzyme activity is assessed by measuring the hydrolysis of [$^3$H]-cyclic AMP, as described by Thompson, W. J., Teraski, W. L., Epstein, P. N., Strada, S. J.: Adv. Cyclic Nucleotide Res. 10:69, 1979. The cyclic AMP concentration used in this assay is 0.2 $\mu$M, which approximates the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

TABLE 2

THIOISOGUANINES - BIOLOGICAL DATA

| Name | Calc IC50 PDE IV |
|------|------------------|
| 3-(cyclopropylmethyl)-3,7-dihydro-8-(1-methyl-ethyl)-6-propylamino-2H-purin-2-one hydrochloride | 23.95 |
| 8-cyclopropyl-3-ethyl-6-ethylamino-3,7-dihydro-2-thio-2H-purin-2-one | 13.65 |
| 8-cyclopropyl-3-ethyl-6-propylamino-2-thio-2H-purin-2-one | 8.48 |
| 3-butyl-8-cyclopropyl-3,7-dihydro-6-ethylamino-2-thio-2H-purin-2-one | 34.86 |
| 3-benzyl-6-ethylamino-3,7-dihydro-8-(i-methylethyl)-2-thio-2H-purin-2-one | 28.37 |
| 3-cyclohexylmethyl-8-cyclopropyl-3,7-dihydro-6-ethylamino-2-thio-2H-purin-2-one | 15.20 |
| 6-benzylamino-8-(cyclopropyl)-3,7-dihydro-3-(propyl)-2-thio-2H-purin-2-one hydrochloride | 33.60 |
| 8-cyclopropyl-3,7-dihydro-3-propyl-6-(4-pyridylmethylamino)-2-thio-2H-purin-2-one | 0.41 |
| 6-cyclopentylamino-8-cyclopropyl-3,7-dihydro-3-propyl-2-thio-2H-purin-2-one hydrochloride | 7.41 |
| 6-butylamino-8-cyclopropyl-3,7-dihydro-3-propyl-2-thio-2H-purin-2-one | 24.48 |
| 8-cyclopropyl-3,7-dihydro-6-(2-hydroxyethylamino)-2-thio-2H-purin-2-one | 4.48 |
| 6-amino-8-cyclopropyl-3,7-dihydro-3-propyl-2-thio-2H-purin-2-one | 39.42 |
| 3-ethy-6-cyclopentylamino-3,7-dihydro-8-isopropyl-2-thio-2H-purine-2-one | 9.40 |
| 6-cyclopentylamino-3,7-dihydro-8-isopropyl-3-propyl-2-thio-2H-purin-2-one | 45.10 |
| 3-ethyl-6-cyclopentylamino-8-cyclopropyl-3,7-dihydro-2-thio-2H-purin-2-one | 0.19 |
| 3-(4-chlorobenzyl)-6-cyclopentylamino-3,7-dihydro-8-isopropyl-2-thio-2H-purine-2-one | 114.50 |

EXAMPLE 12

ADENINE DERIVATIVES

Following the method of the above Examples, the following compounds were similarly prepared from the appropriate starting materials. All temperatures are in ° C. unless otherwise stated.

The data is provided in Table 3 below.

TABLE 3

ADENINES

| Compound | m.p. |
|---|---|
| 6-ethylamino-3-hexyl-3H-purine hydrochloride | 190–195 |
| 3-hexyl-6-methylamino-3H-purine | 142–143 |
| 3-benzyl-6-methylamino-3H-purine | 142–143 |
| 8-cyclopropyl-6-ethylamino-3-(3-methylbutyl)-3H-purine hydrochloride | 188–190 |
| 8-cyclopropyl-3-ethyl-6-propylamino-3H-purine hydrochloride | 186–188 |
| 8-cyclopropyl-3-ethyl-6-methylamino-3H-purine | 143–145 |
| 3-butyl-6-ethylamino-3H-purine | 127–129 |
| 3-butyl-8-cyclopropyl-6-ethylamino-3H-purine | 182–184 |
| 6-ethylamino-3-propyl-3H-purine | 157–159 |
| 8-cyclopropyl-6-ethylamino-3-propyl-3H-purine hydrochloride | 193–195 |
| 8-cyclopropyl-3-cyclopropylmethyl-6-ethylamino-3H-purine hydrochloride | 195–197 |
| 3-benzyl-6-ethylamino-3H-purine | 187–188 |
| 8-cyclopropyl-6-cyclopropylamino-3-propyl-3H-purine hydrochloride | 200–210 |
| 3-((2-methyl)butyl))-6-(2-piperazine-1-yl)ethylamino)-3H-purine | 144–145 |
| 3-cyclohexylmethyl-6-ethylamino-3H-purine hydrochloride | 258–265 |
| 3-benzyl-6-ethylamino-8-(1-methylethyl)-3H-purine hydrochloride | 199–200 |
| 3-cyclohexylmethyl-8-cyclopropyl-6-ethylamino-3H-purine hydrochloride | 192–193 |
| 3-cyclopropylmethyl-8-isopropyl-6-ethylamino-3H-purine | 96–99 |
| 3-ethyl-8-isopropyl-6-benzylamino-3H-purine | 141–142 |
| 3-ethyl-8-isopropyl-6-ethylamino-3H-purine hydrochloride | 194–195 |
| 3-ethyl-8-cyclopentyl-6-benzylamino-3H-purine hydrochloride | 179–182 |
| 3-ethyl-8-cyclopentyl-6-ethylamino-3H-purine hydrochloride | 212–214 |
| 3-(4-chlorobenzyl)-6-ethylamino-3-purine | |
| 3-(4-chlorobenzyl)-6-ethylamino-3H-purine hydrochloride | 251–4 |
| 3-(4-chlorobenzyl)-6-ethylamino-8-isopropyl-3H-purine | |
| 3-(4-chlorobenzyl)-6-ethylamino-8-isopropyl-3H-purine hydrochloride | 215–7 |
| 6-benzylamino-8-cyclopropyl-3-propyl-3H-purine | |
| 8-cyclopropyl-6-hexylamino-3-propyl-3H-purine hydrochloride | |
| 8-cyclopropyl-3-propyl-6-(4-pyridylmethylamino)-3H-purine dihydrochloride | 206–30 |
| 6-cyclopentyl-8-cyclopropyl-3-propyl-3H-purine hydrochloride | 273–6 |
| 6-butylamino-8-cyclopropyl-3-propyl-3H-purine hydrochloride | 171–3 |
| 8-cyclopropyl-6-(2-hydroxyethylamino)-3-propyl-3H-purine | |
| 6-(3-cyclopentyloxy-4-methoxybenzyl-amino)-8-cyclopropyl-3-propyl-3H-purine hydrochloride | |
| 6-amino-8-cyclopropyl-3-propyl-3H-purine | |
| 3-ethyl-6-cyclopentylamino-8-isopropyl-3H-purine hydrochloride | 183–4 |
| 6-cyclohexylamino-8-isopropyl-3-propyl-3H-purlne hydrochloride | 202–3 |
| 6-cyclopentylamino-8-isopropyl-3-propyl-3H-purine hydrochloride | 207–10 |
| 3-ethyl-6-cyclopentylamino-8-cyclopropyl-3H-purine hydrochloride | 205–8 |

TABLE 3-continued

ADENINES

| Compound | m.p. |
|---|---|
| 3-(4-chlorobenzyl)-6-cyclopentylamino-8-cyclopropyl-3H-purine hydrochloride | 269–73 |
| 6-cyclopentylamino-3-(3-cyclopentyl-oxy-4-methoxybenzyl)-8-isopropyl-3H-purine hydrochloride | |
| 3-(2-chlorobenzyl)-6-cyclopentylamino-8-isopropyl-3H-purine hydrochloride | 207–8 |
| 8-cyclopropyl-6-diethylamino-3-propyl-3H-purine hydrochloride | 173–9 |
| 8-cyclopropyl-6-(3-pentylamino)-3-propyl-3H-purine hydrochloride | 187–9 |
| 6-ethylamino-8-isopropyl-3-(4-pyridylmethyl)-3H-purine dihydrochloride | 240–6 |

EXAMPLE 13

ELEMENTAL ANALYSIS OF ADENINES

Elemental analysis was conducted for certain of the compounds set forth in the above tables. The results are provided below.

Elemental analysis for 8-cyclopropyl-3-ethyl-6-ethylamino-3H-purine hydrochloride 99%+1% ($H_2O$; HCl)

| | | | | |
|---|---|---|---|---|
| Calc. | C 53.29 | H 6.80 | N 25.00 | O 0.53 |
| Found | C 52.97 | H 7.01 | N 26.01 | O 0.34 |

Elemental analysis for 6-ethylamino-3-hexyl-3H-purine hydrochloride mp 188–94°

| | | | | |
|---|---|---|---|---|
| Calc. | C 55.02 | H 7.81 | N 24.68 | Cl 12.49 |
| Found | C 55.33 | H 8.05 | N 24.50 | Cl 12.71 |

Elemental analysis for 3-hexyl-6-methylamino-3H-purine hydrochloride mp 190–195°

| | | | | |
|---|---|---|---|---|
| Calc. | C 53.43 | H 7.47 | N 25.96 | Cl 13.14 |
| Found | C 53.70 | H 7.81 | N 25.92 | Cl 13.18 |

Elemental analysis for 3-benzyl-6-methylamino-3H-purine hydrochloride mp 220–236°

| | | | | |
|---|---|---|---|---|
| Calc. | C 56.63 | H 5.12 | N 25.40 | Cl 12.86 |
| Found | C 56.84 | H 5.20 | N 25.21 | Cl 12.84 |

Elemental analysis for 8-cyclopropyl-6-ethylamino-3-(3-methylbutyl)-3H-purine hydrochloride

| | | | | |
|---|---|---|---|---|
| Calc. | C 58.15 | H 7.81 | N 22.60 | Cl 11.44 |
| Found | C 58.12 | H 8.01 | N 22.65 | Cl 11.46 |

Elemental analysis for 8-cyclopropyl-3-ethyl-6-propylamino-3H-purine hydrochloride

| | | | | |
|---|---|---|---|---|
| Calc. | C 55.41 | H 7.15 | N 24.85 | Cl 12.58 |
| Found | C 55.74 | H 7.06 | N 25.08 | Cl 12.71 |

Elemental analysis for 8-cyclopropyl-3-ethyl-6-methylamino-3H-purine

| | | | |
|---|---|---|---|
| Calc. | C 60.81 | H 6.96 | N 32.23 |
| Found | C 60.58 | H 7.02 | N 32.67 |

Elemental analysis for 3-butyl-6-ethylamino-3H-purine hydrochloride mp 221–223°

| | | | | |
|---|---|---|---|---|
| Calc. | C 51.65 | H 7.09 | N 27.38 | Cl 13.88 |
| Found | C 51.74 | H 7.06 | N 27.62 | Cl 13.93 |

Elemental analysis for 3-butyl-8-cyclopropyl-6-ethylamino-3H-purine hydrochloride mp 194–196°

| | | | | |
|---|---|---|---|---|
| Calc. | C 56.83 | H 7.49 | N 23.67 | Cl 11.98 |
| Found | C 56.91 | H 6.98 | N 23.97 | Cl 12.03 |

Elemental analysis for 6-ethylamino-3-propyl-3H-purine

98%+2% water

| | | | |
|---|---|---|---|
| Calc. | C 57.35 | H 7.44 | N 33.44 |
| Found | C 57.68 | H 7.22 | N 33.29 |

Elemental analysis for 8-cyclopropyl-6-ethylamino-3-propyl-3H-purine hydrochloride

| | | | | |
|---|---|---|---|---|
| Calc. | C 55.41 | H 7.15 | N 24.85 | Cl 12.58 |
| Found | C 55.45 | H 7.13 | N 24.96 | Cl 12.71 |

Elemental analysis for 8-cyclopropyl-3-cyclopropylmethyl-6-ethylamino-3H-purine hydrochloride

| | | | | |
|---|---|---|---|---|
| Calc. | C 57.23 | H 6.87 | N 23.84 | Cl 12.07 |
| Found | C 57.49 | H 6.88 | N 23.59 | Cl 12.49 |

Elemental analysis for 3-benzyl-6-ethylamino-3H-purine

| | | | |
|---|---|---|---|
| Calc. | C 66.39 | H 5.97 | N 27.65 |
| Found | C 66.58 | H 5.63 | N 27.80 |

Elemental analysis for 8-cyclopropyl-6-cyclopropylamino-3-propyl-3H-purine hydrochloride

| | | | | |
|---|---|---|---|---|
| Calc. | C 57.23 | H 6.86 | N 23.84 | Cl 12.07 |
| Found | C 57.30 | H 6.90 | N 23.77 | Cl 12.16 |

Elemental analysis for 3-cyclohexylmethyl-6-ethylamino-3H-purine hydrochloride

| | | | | |
|---|---|---|---|---|
| Calc. | C 56.84 | H 7.50 | N 23.67 | Cl 11.98 |
| Found | C 56.82 | H 7.54 | N 23.65 | Cl 12.05 |

Elemental analysis for 3-benzyl-6-ethylamino-8-(1-methylethyl)-3H-purine hydrochloride

| | | | | |
|---|---|---|---|---|
| Calc. | C 61.52 | H 6.68 | N 21.10 | Cl 10.68 |
| Found | C 61.52 | H 6.59 | N 21.18 | Cl 10.60 |

Elemental analysis for 3-cyclohexylmethyl-8-cyclopropyl-6-ethylamino-3H-purine hydrochloride

| | | | | |
|---|---|---|---|---|
| Calc. | C 60.79 | H 7.80 | N 20.85 | Cl 10.56 |
| Found | C 60.55 | H 7.48 | N 20.85 | Cl 11.34 |

Elemental analysis for 3-ethyl-8-isopropyl-6-ethylamino-3H-purine hydrochloride

| | | | |
|---|---|---|---|
| Calc. | C 53.43 | H 7.47 | N 25.96 |
| Found | C 53.62 | H 7.66 | N 25.34 |

Elemental analysis for 6-benzylamino-8-cyclopentyl-3-ethyl-3H-purine hydrochloride

| | | | |
|---|---|---|---|
| Calc. | C 63.78 | H 6.76 | N 19.57 |
| Found | C 63.55 | H 6.54 | N 19.51 |

Elemental analysis for 8-cyclopentyl-3-ethyl-6-ethylamino-3H-purine hydrochloride

| Calc. | C 56.84 | H 7.50 | N 23.67 |
|---|---|---|---|
| Found | C 56.54 | H 7.37 | N 23.63 |

EXAMPLE 14

PDE IV INHIBITION BY ADENINE COMPOUNDS

The PDE IV inhibitory effect of certain of the compounds set forth above was examined according to the methods previously described. The results are provided in Table 4 below.

TABLE 4

PDE IV RESULTS

| Compound | calc PDE IV IC50 ($\mu$M) |
|---|---|
| 3-ethyl-8-isopropyl-6-ethylamino-3H-purine hydrochloride | 52.17 |
| 3-ethyl-8-cyclopentyl-6-benzylamino-3H-purine hydrochloride | 62.44 |
| 3-ethyl-8-cyclopentyl-6-ethylamino-3H-purine hydrochloride | 28.34 |
| 3-cyclohexylmethyl-6-ethylamino-3H-purine hydrochloride | 32.95 |
| 3-cyclohexylmethyl-8-cyclopropyl-6-ethylamino-3H-purine hydrochloride | 3.78 |
| 8-cyclopropyl-6-ethylamino-3-(3-methylbutyl)-3H-purine hydrochloride | 2.45 |
| 8-cyclopropyl-3-ethyl-6-propylamino-3H-purine hydrochloride | 15.67 |
| 8-cyclopropyl-3-cyclopropylmethyl-6-ethylamino-3H-purine hydrochloride | 4.11 |
| 3-hexyl-6-methylamino-3H-purine hydrochloride | 34.15 |
| 3-cyclopropylmethyl-8-isopropyl-6-ethylamino-3H-purine hydrochloride | 12.66 |
| 3-ethyl-8-isopropyl-6-benzylamino-3H-purine hydrochloride | 28.94 |
| 3-butyl-6-ethylamino-3H-purine hydrochloride | 66.41 |
| 3-butyl-8-cyclopropyl-6-ethylamino-3H-purine hydrochloride | 5.99 |
| 8-cyclopropyl-6-ethylamino-3-propyl-3H-purine hydrochloride | 6.31 |
| 8-cyclopropyl-6-cyclopropylamino-3-propyl-3H-purine hydrochloride | 7.90 |
| 3-(3-cyclopentyloxy-4-methoxybenzyl)-6-ethylamino-8-isopropyl-3H-purine hydrochloride | 0.32 |
| 3-(4-chlorobenzyl)-6-ethylamino-3H-purine hydrochloride | 37.75 |
| 3-ethyl-6-ethylamino-8-((3-cyclopentyloxy-4-methoxy)benzyl)-3H-purine hydrochloride | 4.52 |

EXAMPLE 15

Dithioxanthine derivatives of the present invention were manufactured and analyzed. The results are set forth in Table 5 below.

TABLE 5

DITHIOXANTHINES

| Compound | m.p. | IC50 PDE IV |
|---|---|---|
| 3,7-dihydro-3-ethyl-2,6-dithio-1H-purine-2,6-dione | 275–276 | |
| 3,7-dihydro-3-propyl-2,6-dithio-1H-purine-2,6-dione | 294–297 | |
| 3,7-dihydro-8-ethyl-3-propyl-2,6-dithio-1H-purine-2,6-dione | 266–267 | |
| 3-butyl-3,7-dihydro-2,6-dithio-1H-purine-2,6-dione | 249–251 | |
| 3-butyl-3,7-dihydro-8-ethyl-2,6-dithio-1H-purine-2,6-dione | 251–252 | |
| 3,7-dihydro-3,8-diethyl-2,6-dithio-1H-purine-2,6-dione | 260–261 | |
| 3-benzyl-3,7-dihydro-2,6-dithio-1H-purine-2,6-dione | 298–303 | 38.49 |
| 3,7-dihydro-3-hexyl-2,6-dithio-1H-purine-2,6-dione | 222–224 | |
| 8-cyclopropyl-3,7-dihydro-3-(3-methylbutyl)-2,6-dithio-1H-purine-2,6-dione | | 6.31 |
| 8-cyclopropyl-3,7-dihydro-3-ethyl-2,6-dithio-1H-purine-2,6-dione | | 6.18 |
| 3,7-dihydro-3-(2-methylbutyl)-2,6-dithio-1H-purine-2,6-dione | | |
| 3-butyl-8-cyclopropyl-3,7-dihydro-2,6-dithio-1H-purine-2,6-dione | | 9.43 |
| 3-cyclopropylmethyl-3,7-dihydro-2,6-dithio-1H-purine-2,6-dione | | |
| 8-cyclopropyl-3,7-dihydro-3-propyl-2,6-dithio-1H-purine-2,6-dione | | 64.49 |
| 8-isopropyl-3-(4-pyridylmethyl)-2,6-dithio-1H-purine-2,6-dione | 310–315 | |

EXAMPLE 16

PHARMACOLOGICAL TESTS

Isolated Guinea Pig Trachea

The test compound was dissolved in dimethylsulfoxide. Guinea pig isolated trachealis muscle was mounted in a bath containing Krebs solution maintained at 37.5° C. and bubbled with carbogen (95% $O_2$, 5% $CO_2$).

Tension changes were recorded isometrically using force displacement transducers in conjunction with potentiometric pen recorders.

The ability of the test compounds to relax airways muscle was investigated by the construction of cumulative concentration effect curves. Each concentration of the test compound was allowed to equilibrate with the tissue for 5 minutes before a concentration increment (ten-fold) was made.

In each tissue the test compound was compared with theophylline as standard.

| Compound | In Vitro Activity |
| --- | --- |
| Theophylline | 1 |
| 8-Cyclopropyl-3-ethyl-6-ethylamino-3H-purine | 43.7 |
| 6-Ethylamino-3-hexyl-3H-purine | 25.6 |
| 3-Benzyl-6-ethylamino-3H-purine | 18.5 |

EXAMPLE 17

IN-VIVO STUDIES (i) The effect of test compounds in a model of bronchial hyperresponsiveness (BHR) and cellular infiltration in the guinea pig induced by ovalbumin (see, for example Morley et al, Agents and Actions, Supplement, 1988, 23, 187) were studied.

The test compound was administered at doses of 0.5 and 1.0 mg/kg/day given subcutaneously over 7 days by osmotic mini-pump. Theophylline and salbutamol at concentrations of 1 mg/kg/day were used as standards. Dose response curves to histamine (1–50 μg/kg) were constructed for each animal.

Figure 2:
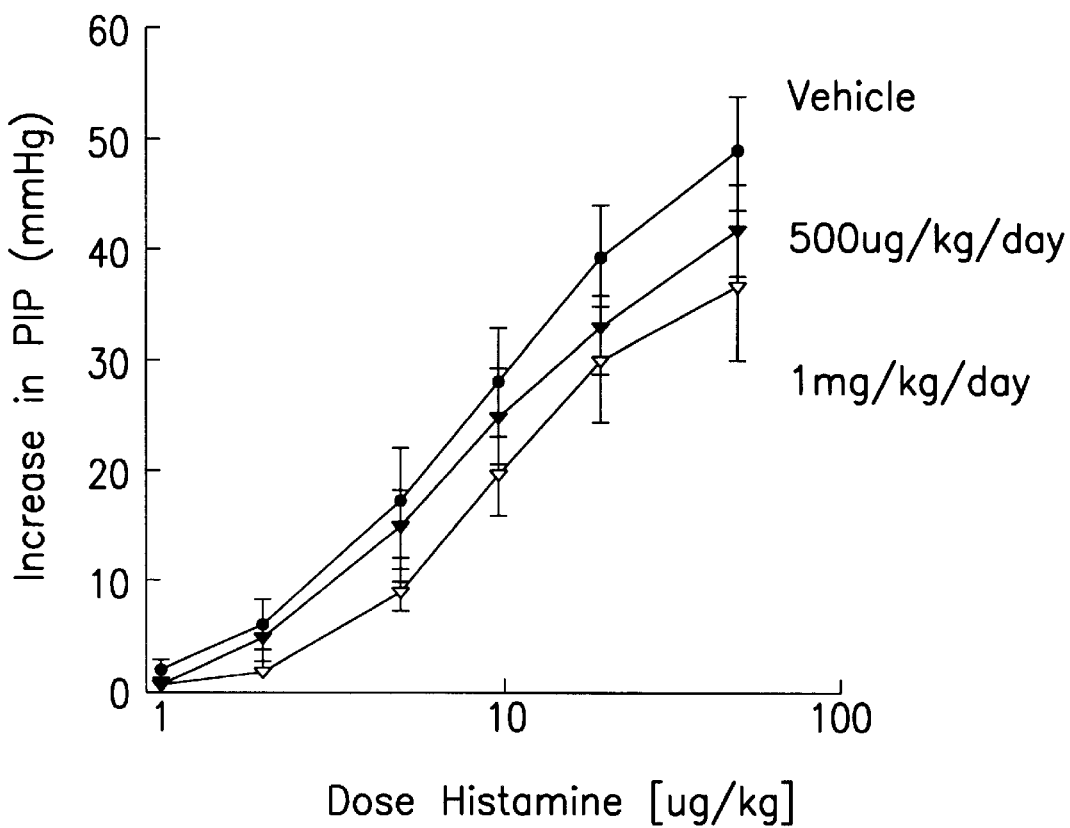
FIG. 2 shows dose response curves to histamine in a test animal after administration of 6-ethylamino-3-hexyl-3H-purine at doses of 0.5 and 1.0 mg/kg/day given subcutaneously over 7 days by osmotic mini-pump.

FIGS. 1–2 show the results obtained.

(ii) Sensitization and Challenge procedure: Male Dunkin Hartley guine pigs (Charles River) (200–250 g) were injected i.p. with ovalbumin (OVA) (0.5 ml/animal; 20 μg OVA in Al(OH)$_3$ (moist gel)); this preparation produced an injectable stable suspension containing excess Al(OH)$_3$. Sham animals were injected with 0.5 ml Al(OH)$_3$ alone. After a period of 18–21 days animals were exposed to an aerosol of OVA (100 μg/ml) for 1 hour in an exposure chamber.

(iii) Bronchoalveolar lavage: Animals were anaesthetized, 24 hours after aerosol exposure, with urethane (25%, w/v, 7 ml/kg, i.p.) and the trachea cannulated. Bronchoalveolar lavage (BAL) was performed by instilling 5 ml sterile saline into the lungs via the tracheal cannula and the fluid was immediately removed. The fluid was reinjected and the procedure repeated 5 times in total. This procedure resulted in a 40–60% recovery of BAL fluid from the lungs of the guinea pig. Total cell counts were perfomed on the resultant BAL fluid using an improved Neubauer haemocytometer. Cytospin preparations were prepared using a Shandon Cytospin 2 centrifuge. Two drops of BAL fluid were added to each cytospin cup and the samples were centrifuged for 1 min at 1300 r.p.m. Slides were fixed in acetone and stained with haemotoxylin and carbol chromotrope according to the method described by Lendrum (Lendrum 1944), differential cell counts were performed on each slide by counting 200 cells at random, the cell types were classified as neutrophils, eosinophils and mononuclear cells according to standard morphological criteria. Cells were counted blind. The results are expressed as the number of neutrophils, eosinophils and mononuclear cells per ml of BAL fluid. The remaining BAL fluid was centrifuged (10 min., 1000 g) and the resultant cells and cell free supernatants were aliquotted and frozen for later assays. Compounds were solubilized in either DMSO or saline administered intraperitoreally at a dose of 5 mg/kg one hour prior to ovalbumin challenge. The results are provided below in Table 6.

TABLE 6

| Compound | N | Dose mg/kg ip | % Eosinophils in BAL x ± se | % Inhibition |
| --- | --- | --- | --- | --- |
| DMSO Vehicle | 9 | — | 32 ± 6 | — |
| 3-(3-cyclopentyloxy-4-methoxybenzyl)-3,7-dihydro-8-isopropyl-2,6-dithio-1H-purin-2,6-dione | 6 | 5 | 17 ± 3 | 47% |
| Saline Vehicle | 14 | — | 33 ± 3 | — |
| 8-cyclopropyl-6-ethylamino-3-(3-methyl-butyl)-3H-purine hydrochloride | 7 | 5 | 16 ± 4 | 52% |
| 3-(3-cyclopentyloxy-4-methoxy-benzyl)-6-ethylamino-8-isopropyl-3H-purine hydrochloride | 7 | 5 | 12 ± 2 | 64% |

While the invention has been illustrated with respect to the production and use of a particular compound, it is apparent that variations and modifications of the invention can be made without departing from the spirit or scope of the invention.

What is claimed is:

1. A compound selected from the group consisting of 8-cyclopropyl-6-ethylamino-3-(3-methylbutyl)-3H-purine, 8-cyclopropyl-3-ethyl-6-propylamino-3H-purine; 8-cyclopropyl-3ethyl-6-methylamino-3H-purine; 3-butyl-8-cyclopropyl-6-ethylamino-3H-purine; 8-cyclopropyl6-ethylamino-3-propyl-3H-purine; 8-cyclopropyl-3-cyclopropylmethyl-6-ethylamino-3H-purine; 8-cyclopropyl-6-cyclopropylamino-3-propyl-3H-purine; 3-benzyl-6-ethylamino-8-(1-methylethyl)-3H-purine; 3-cyclohexylmethyl-8-cyclopropyl-6-ethylamino-3H-purine; 3-cyclopropylmethyl-8-isopropyl-6-ethylamino-3H-purine; 3-ethyl-8-isopropyl-6-benzylamino-3H-purine; 3-ethyl-8-isopropyl-6-ethylamino-3H-purine; 3-ethyl-8-cyclopentyl-6-benzylamino-3H-purine; 3-ethyl-8-cyclopentyl-6-ethylamino-3H-purine; 3-(4-chlorobenzyl)-6-ethylamino-8-isopropyl-3H-purine; 6-benzylamino-8-cyclopropyl-3-propyl-3H-purine; 8-cyclopropyl-6-hexylamino-3-propyl-3H-purine; 8-cyclopropyl-3-propyl-6-(4-pyridylmethylamino)-3H purine; 6-cyclopentylamino-8-cyclopropyl-3-propyl-3H-purine; 6-butylamino-8-cyclopropyl-3-propyl-3H-purine; 8-cyclopropyl-6-(2-hydroxyethylamino)-3-propyl-3H-purine; 6-(3-cyclopentyloxy-4-methoxybenzylamino)-8-cyclopropyl-3-propyl-3H-purine; 3-ethyl-6-cyclopentylamino-8-isopropyl-3H-purine; 6-cyclohexylamino-8-isopropyl-3-propyl-3H-purine; 6-cyclopentylamino-8-isopropyl-3-propyl-3H-purine; 3-ethyl-6-cyclopentylamino-8-cyclopropyl-3H-purine; 3-(4-chlorobenzyl)-6-cyclopentylamino-8-cyclopropyl-3H-purine; 6-cyclopentylamino-3-(3-cyclopentyloxy-4-methoxybenzyl)-8-isopropyl-3H-purine; 3-(2-chlorobenzyl)-6-cyclopentylamino-8-isopropyl-3H-purine; 8-cyclopropyl-6-diethylamino-3-propyl-3H-purine;

8-cyclopropyl-6-(3-pentylamino)-3-propyl-3H-purine; 6-ethylamino-8-isopropyl-3-(4-pyridylmethyl)-3H-purine; 3-ethyl-8-isopropyl-6-ethylamino-3H-purine; 3-ethyl-8-cyclopentyl-6-benzylamino-3H-purine; 3-ethyl-8-cyclopentyl-6-ethylamino-3H-purine; 3-cyclohexylmethyl-8-cyclopropyl-6-ethylamino-3H-purine; 8-cyclopropyl-6-ethylamino-3-(3-methylbutyl)-3H-purine; 8-cyclopropyl-3-ethyl-6-propylamino-3-H-purine; 8-cyclopropyl-3cyclopropylmethyl-6-ethylamino-3H purine; 3-cyclopropylmethyl-8-isopropyl-6-ethylamino-3H-purine; 3-ethyl-8-isopropyl-6-benzylamino-3H-purine; 3-butyl-8-cyclopropyl-6-ethylamino-3H-purine; 8-cyclopropyl-6-ethylamino-3-propyl-3H-purine; 8-cyclopropyl-6-cyclopropylamino-3-propyl-3H-purine; 3-(3-cyclopentyloxy-4-methoxybenzyl)-6-ethylamino-8-isopropyl-3H-purine; 3-ethyl-6-ethylamino-8-(3-cyclopentyloxy-4-methoxy-benzyl)-3H-purine; and pharmaceutically acceptable salts thereof.

2. A compound of claim 1, which is selected from the group consisting of 3-(4-chlorobenzyl)-6-ethylamino-8-isopropyl-3H-purine; 3-(3-cyclopentyloxy-4-methoxybenzyl)-6-ethylamino-8-isopropyl-3H-purine; 6-cyclopentylamino-8-cyclopropyl-3-propyl-3H-purine, and pharmaceutically acceptable salts thereof.

3. A compound selected from the group consisting of
3-(2-methylbutyl))-6-3H-purine;
3-cyclohexylmethyl-6-ethylamino-3H-purine;
3-(4-chlorobenzyl)-6-ethylamino-3H-purine; and
3-(3-cyclopentyloxy-4-methoxybenzyl)-6-ethylamino-3 H-purine;
and pharmaceutically acceptable salts thereof.

4. The compound of claim 1 that is 8-cyclopropyl-6-ethylamino-3-(3-methylbutyl)-3H-purine and pharmaceutically acceptable salts thereof.

5. The compound of claim 1 that is 8-cyclopropyl-3-cyclopropylmethyl-6-ethylamino-3H-purine and pharmaceutically acceptable salts thereof.

6. The compound of claim 1 that is 3-ethyl-8-isopropyl-6-benzylamino-3H-purine and pharmaceutically acceptable salts thereof.

7. The compound of claim 2 that is 3-(4-chlorobenzyl)-6-ethylamino-3H-purine and pharmaceutically acceptable salts thereof.

8. The compound of claim 1 that is 3-(4-chlorobenzyl)-6-ethylamino-8-isopropyl-3H-purine and pharmaceutically acceptable salts thereof.

9. The compound of claim 1 that is 8-cyclopropyl-3-propyl-6-(4-pyridylmethylamino)-3H-purine and pharmaceutically acceptable salts thereof.

10. The compound of claim 1 that is 6-cyclopentylamino-8-cyclopropyl-3-propyl-3H-purine and pharmaceutically acceptable salts thereof.

11. The compound of claim 1 that is 6-(3-cyclopentyloxy-4-methoxy-benzylamino)-8-cyclopropyl-3-propyl-3H-purine and pharmaceutically acceptable salts thereof.

12. The compound of claim 1 that is 3-(4-chlorobenzyl)-6-cyclopentylamino-8-cyclopropyl-3H-purine and pharmaceutically acceptable salts thereof.

13. The compound of claim 1 that is 6-cyclopentylamino-3-(3-cyclopentyloxy-4-methoxybenzyl)-8-isopropyl-3H-purine and pharmaceutically acceptable salts thereof.

14. The compound of claim 1 that is 6-ethylamino-8-isopropyl-3-(4-pyridylmethyl)-3H-purine and pharmaceutically acceptable salts thereof.

15. The compound of claim 1 that is 3-(3-cyclopentyloxy-4-methoxybenzyl)-6-ethylamino-8-isopropyl-3H-purine and pharmaceutically acceptable salts thereof.

16. The compound of claim 1 that is 3-ethyl-6-ethylamino-8-(3-cyclopentyloxy-4-methoxy-benzyl)-3H-purine and pharmaceutically acceptable salts thereof.

17. The compound of claim 3 that is 3-(3-cyclopentyloxy-4-methoxybenzyl)-6-ethylamino-3H-purine.

18. The compound of claim 1 that is 8-cyclopropyl-3-ethyl-6-propylamino-3H-purine and pharmaceutically acceptable salts thereof.

19. The compound of claim 1 that is 8-cyclopropyl-3-ethyl-6-methylamino-3H-purine and pharmaceutically acceptable salts thereof.

20. The compound of claim 1 that is 3-butyl-8-cyclopropyl-6-ethylamino-3H-purine and pharmaceutically acceptable salts thereof.

21. The compound of claim 1 that is 8-cyclopropyl-6-ethylamino-3-propyl-3H-purine and pharmaceutically acceptable salts thereof.

22. The compound of claim 1 that is 8-cyclopropyl-6-cyclopropylamino-3-propyl-3H-purine and pharmaceutically acceptable salts thereof.

23. The compound of claim 1 that is 3-benzyl-6-ethylamino-8-(1-methylethyl)-3H-purine and pharmaceutically acceptable salts thereof.

24. The compound of claim 1 that is 3-cyclohexylmethyl-8-cyclopropyl-6-ethylamino-3H-purine and pharmaceutically acceptable salts thereof.

25. The compound of claim 1 that is 3-cyclopropylmethyl-8-isopropyl-6-ethylamino-3H-purine and pharmaceutically acceptable salts thereof.

26. The compound of claim 1 that is 3-ethyl-8-isopropyl-6-ethylamino-3H-purine and pharmaceutically acceptable salts thereof.

27. The compound of claim 1 that is 3-ethyl-8-cyclopentyl-6-benzylamino-3H-purine and pharmaceutically acceptable salts thereof.

28. The compound of claim 1 that is 3-ethyl-8-cyclopentyl-6-ethylamino-3H-purine and pharmaceutically acceptable salts thereof.

29. The compound of claim 1 that is 6-benzylamino-8-cyclopropyl-3-propyl-3H-purine and pharmaceutically acceptable salts thereof.

30. The compound of claim 1 that is 8-cyclopropyl-6-hexylamino-3-propyl-3H-purine and pharmaceutically acceptable salts thereof.

31. The compound of claims 1 that is 6-butylamino-8-cyclopropyl-3-propyl-3H-purine and pharmaceutically acceptable salts thereof.

32. The compound of claim 1 that is 8-cyclopropyl-6-(2-hydroxyethylamino)-3-propyl-3H-purine and pharmaceutically acceptable salts thereof.

33. 6-amino-8-cyclopropyl-3-propyl-3H-purine and pharmaceutically acceptable salts thereof.

34. The compound of claim 1 that is 3-ethyl-6-cyclopentylamino-8-isopropyl-3H-purine and pharmaceutically acceptable salts thereof.

35. The compound of claim 1 that is 6-cyclohexylamino-8-isopropyl-3-propyl-3H-purine and pharmaceutically acceptable salts thereof.

36. The compound of claim 1 that is 6-cyclopentylamino-8-isopropyl-3-propyl-3H-purine and pharmaceutically acceptable salts thereof.

37. The compound of claim 1 that is 3-ethyl-6-cyclopentylamino-8-cyclopropyl-3H-purine and pharmaceutically acceptable salts thereof.

38. The compound of claim 1 that is 3-(2-chlorobenzyl)-6-cyclopentylamino-8-isopropyl-3H-purine and pharmaceutically acceptable salts thereof.

39. The compound of claim 1 that is 8-cyclopropyl-6-diethylamino-3-propyl-3H-purine and pharmaceutically acceptable salts thereof.

40. The compound of claim 1 that is 8-cyclopropyl-6-(3-pentylamino)-3-propyl-3H-purine and pharmaceutically acceptable salts thereof.

41. The compound of claim 1 that is 8-cyclopropyl-3-ethyl-6-propylamino-3H-purine and pharmaceutically acceptable salts thereof.

42. A pharmaceutical dosage form for oral administration comprising 3-(3-cyclopentyloxy-4-methoxybenzyl)-6-ethylamino-8-isopropryl-3H-purine or a pharmaceutically acceptable salt thereof together with pharmaceutically acceptable inert excipients.

43. A pharmaceutical composition comprising the compound of claim 11 and a pharmaceutically acceptable carrier.

44. A pharmaceutical composition comprising a compound of claim 1 and a pharmaceutically acceptable carrier.

45. The pharmaceutical composition of claim 44 which is suitable for oral administration.

46. The pharmaceutical composition of claim 44 which is suitable for parenterall administration.

47. The pharmaceutical composition of claim 44 which is suitable for administration by inhalation.

48. The pharmaceutical composition of claim 43 which is suitable for administration by inhalation.

49. The pharmaceutical composition of claim 43 which is suitable for oral administration.

50. The pharmaceutical composition of claim 43 which is suitable for parenteral administration.

* * * * *